United States Patent [19]

Ravetch et al.

[11] Patent Number: 5,824,487

[45] Date of Patent: Oct. 20, 1998

[54] METHOD FOR SCREENING FOR TARGETS FOR ANTI-INFLAMMATORY OR ANTI-ALLERGIC AGENTS

[75] Inventors: Jeffrey V. Ravetch, New York, N.Y.; Tomohiro Kurosaki, Fort Lee, N.J.

[73] Assignee: Sloan-Kettering Institute for Cancer Research, New York, N.Y.

[21] Appl. No.: 542,686

[22] Filed: Oct. 13, 1995

Related U.S. Application Data

[63] Continuation of Ser. No. 52,269, Apr. 23, 1993, abandoned.

[51] Int. Cl.$^6$ .................. G01N 33/53; G01N 33/567; G01N 33/536; C07K 7/08

[52] U.S. Cl. .................. 435/7.8; 435/7.1; 435/7.21; 435/7.24; 435/7.4; 530/300; 530/327; 530/350; 530/827; 530/388.1; 530/389.1; 530/395; 530/402; 530/412; 530/413; 436/501; 436/503; 436/518; 436/536

[58] Field of Search .................................. 435/7.1, 7.21, 435/7.24, 7.4, 7.8; 530/300, 327, 350, 827, 388.1, 389.1, 395, 402, 412, 413; 436/501, 503, 518, 536

[56] References Cited

PUBLICATIONS

Clark, M., et al. (1992) The B Cell Antigen Receptor Complex: Association of Ig–α and Ig–β with Distinct Cytoplasmic Effectors. *Science*, 258: 123–126.

Eiseman, E. et al. (1992) Signal Transduction by the Cytoplasmic Domains of FCεRI–γ and TCR–ζ in Rat Basophilic Leukemia Cells. *The Journal of Biological Chemistry*, 267: 21027–21032.

Irving, B. et al. (1991) The Cytoplasmic Domain of the T Cell Receptor ζ Chain Is Sufficient to Couple to Receptor–Associated signal Transduction Pathways. *Cell*, 64:891–901.

Karnitz, L., et al. (1992) Effects of p. 56$^{lcK}$ Deficiency on the Growth and Cytolytic Effector Function of an Interleukin–2–Dependent Cytotoxic T–Cell Line. *Molecular and Cellular Biology*, 12:4521–4530.

Letourneur, F. et al. (1991) T–cell and basophil activation through the cytoplasmic tail of T–cell receptor ζ family proteins. *Proc Natl. Acad. Sci, USA*, 88:8905–8909.

Orloff, G. et al. (1990) Family of disulphide–linked dimers containing the ζ and η chains of the T–cell receptor and the γ chain of Fc receptors. *Nature*, 347: 189–191.

Romeo, C. et al. (1991) Cellular Immunity to HIV Activated by CD4 Fused to T Cell or Fc Receptor Polypeptides. *Cell*, 64:1037–1046.

Straus, D. et al. (1992) Genetic Evidence for the Involvement of the lck Tyrosine Kinase in Signal Transduction through the T Cell Antigen Receptor *Cell*, 70:585–593.

Edsington, Bio/Technology, 10: 383–389, 1992.

*Primary Examiner*—Ronald B. Schwadron
*Attorney, Agent, or Firm*—John P. White

[57] ABSTRACT

This invention provides a method for identifying a cellular protein capable of specifically binding to an activated antibody receptor, whose cytoplasmic domain comprising an ARH1 motif, comprising (a) obtaining cells comprising receptors having the ARH1 motif; (b) lysing the cells under conditions whereby the native complex of the receptor having the ARH1 motif and the cellular protein is preserved; (c) isolating the complex; and (d) testing the associated receptor and the protein for biochemical activities, thereby identifying the cellular protein capable of specifically binding to an activated antibody receptor, whose cytoplasmic domain comprising an ARH1 motif. This invention further provides a method for identifying a cellular molecule capable of being a target for designing drugs for autoimmune disease, inflammation or allergy which comprises (a) contacting a cell lysate with a molecule having a motif of amino acid sequence, AENTITYSLLKHP under the conditions permitting formation of a complex between the cellular target molecule with the motif; (b) isolating the complex formed in step (a); and (c) testing the complex for biochemical activities, thereby identifying the cellular molecule capable of being a target for designing drugs for autoimmune disease, inflammation or allergy.

9 Claims, 20 Drawing Sheets

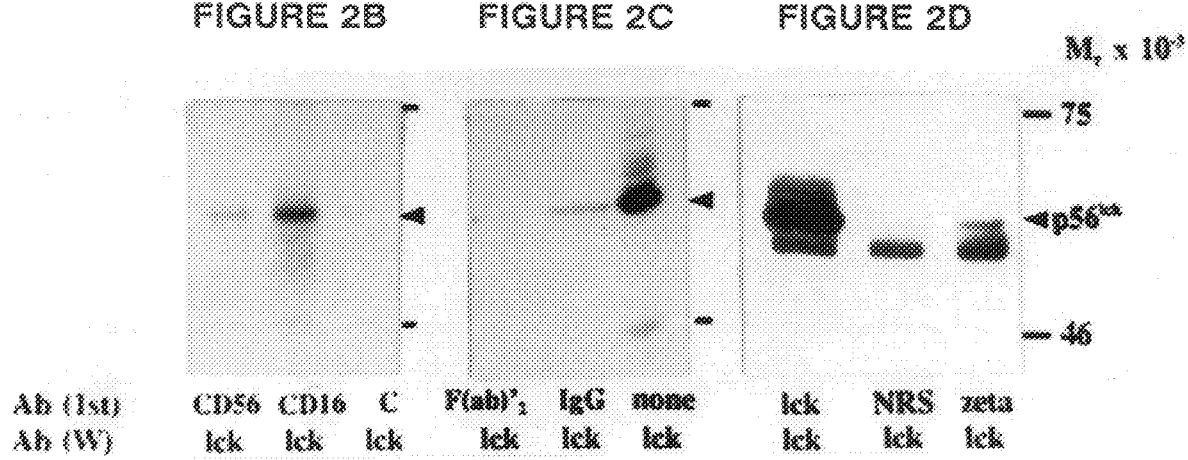

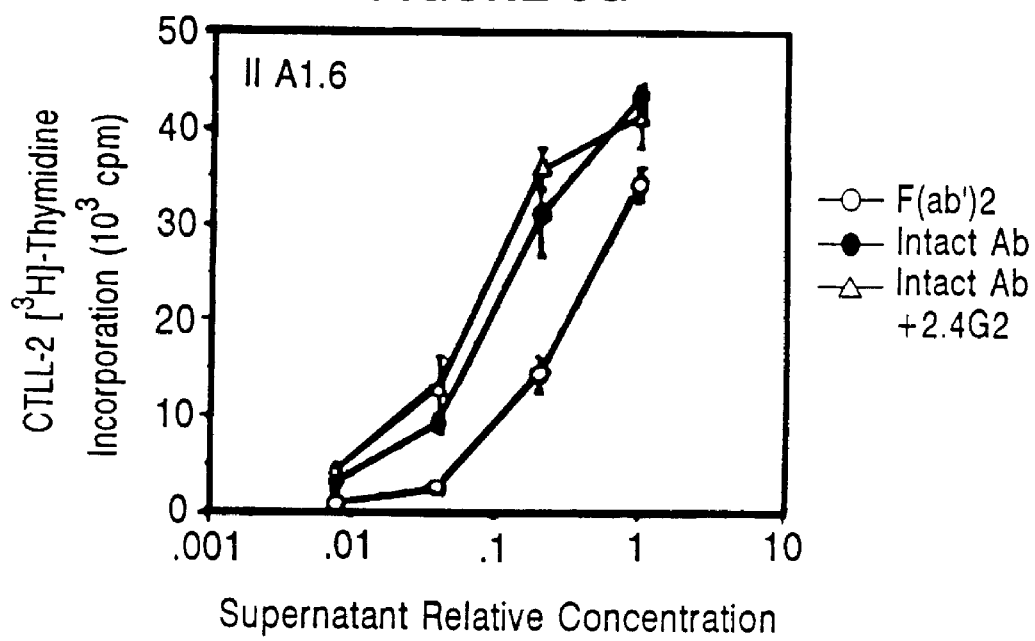
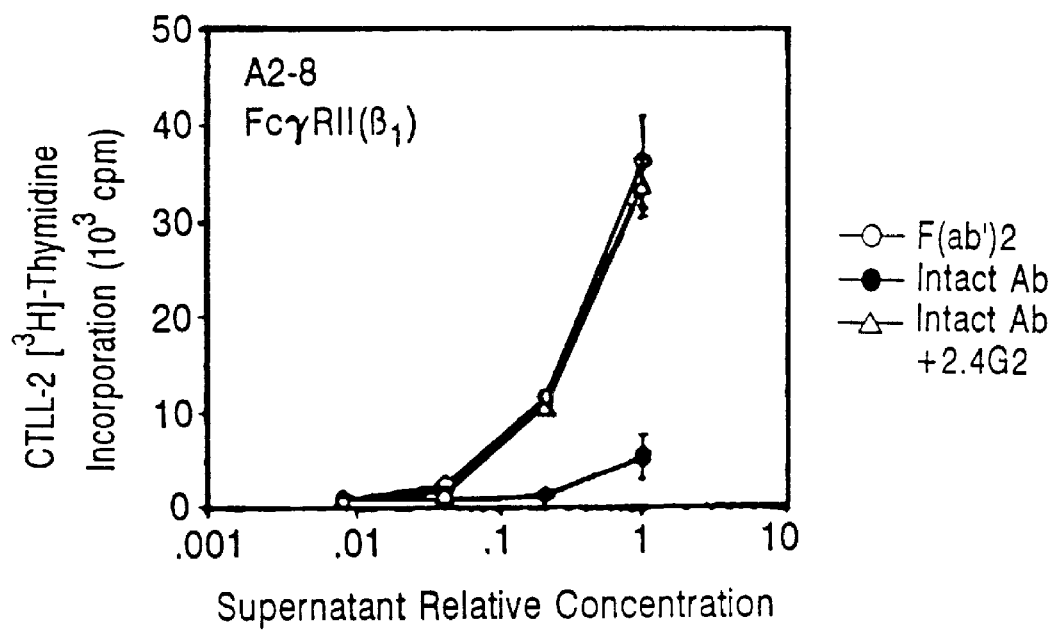

IgM/Igβ

IgM/Igα

IgM/Igβ

IgM/Igα

IgM/Igβ

IgM/Igα

METHOD FOR SCREENING FOR TARGETS FOR ANTI-INFLAMMATORY OR ANTI-ALLERGIC AGENTS

This application is a continuation of U.S. Ser. No. 08/052,269, filed Apr. 23, 1993, now abandoned.

This invention was made with support under National Institute of Health Grant No. GM 39256. Accordingly, the U.S. government has certain rights in the invention.

BACKGROUND OF THE INVENTION

Throughout this application various references are referred to within parentheses. Disclosures of these publications in their entireties are hereby incorporated by reference into this application to more fully describe the state of the art to which this invention pertains. Full bibliographic citations for these references may be found at the end of each series of experiments.

The interaction of antibody-antigen complex with cells of the immune system results in a wide array of responses, ranging from effector functions such as antibody-dependent cytotoxicity, mast cell degranulation, and phagocytosis to immunomodulatory signals such as regulating lymphocyte proliferation and antibody secretion. All these interactions are initiated through the binding of the Fc domain of antibodies or immune complexes to specialized cell surface receptors on hematopoietic cells. It is now well established that the diversity of cellular responses triggered by antibodies and immune complexes results from the structural heterogeneity of Fc receptors. Considerable progress has been made in the last several years in defining this heterogeneity for IgG and IgE Fc receptors (FcγR, FcεR) through their molecular cloning. Those studies make it apparent that Fc receptors share structurally related ligand binding domains, but differ in their transmembrane and intracellular domains which presumably mediate intracellular signalling. Thus, specific FcγRs and FcεR has also revealed at least one common subunit among some of these receptors.

It was recently observed that a family of disulfide-linked dimers are shared by Fc receptors and the T cell antigen receptor (TCR). Comparison of the genes for FcεRI (FcγRIII)γ and TCRζ chain indicates that they belong to the same family and have been generated by duplication. Both genes are located on mouse and human chromosome 1 and show an analogous organization of their exons. In both genes, the leader peptide is encoded by two exons, the second of which also contains the short extracellular domain, the hydrophobic transmembrane region, and the beginning of the cytoplasmic tail. The following exons, exons 3–5 and exons for γ and ζ, respectively, encode the remainder of the cytoplasmic tail. Furthermore, a high level of homology between the two genes is found in three of their respective exons, at the DNA and protein level (both about 50%). Finally, both γ and ζ polypeptides use homologous cysteines essential for the surface expression of their respective receptors.

The detection of transcripts for ζ chains in TCR-, CD3-NK cells led to the finding that human FcγRIIIAα from NK cells physically associates with ζ-ζ homodimer and with ζ-γ heterodimer. So far, three different dimers have been identified in Fc receptor complexes: γ-γ ζ-ζ and ζ-γ. These dimers are also part of the TCR complex and probably mediate similar functions. There is a third member of the same family, TCRη which is generated by alternate splicing from the same gene as TCRζ. The dimers η-η, η-ζ, and η-γ apparently are only associated with TCR, and so far there is no evidence that they associate with Fc receptor structures. Possibly, new members of the same family will be identified that form part of Fc receptor complexes.

SUMMARY OF THE INVENTION

This invention provides a method for identifying a cellular protein capable of specifically binding to an activated antibody receptor, whose cytoplasmic domain comprising an ARH1 motif, comprising (a) obtaining a cell lysate;(b) contacting the cell lysate with a molecule having an ARH1 motif under the conditions permitting formation of a complex between the cellular protein and the molecule; (c) isolating the complex formed in step (b); (d) testing the complex for biochemical activities, thereby identifying the cellular protein capable of specifically binding to an activated antibody receptor, whose cytoplasmic domain comprising the ARH1 motif.

This invention also provides a method for identifying a cellular protein capable of specifically binding to an activated antibody receptor, whose cytoplasmic domain comprising an ARH1 motif, comprising (a) obtaining cells comprising receptors having the ARH1 motif; (b) lysing the cells under conditions whereby the native association of the receptor having the ARH1 motif and the cellular protein is preserved;(c) identifying the associated receptor containing the ARH1 motif and the cellular protein; and (d) testing the associated receptor and the protein for biochemical activities, thereby identifying the cellular protein capable of specifically binding to an activated antibody receptor, whose cytoplasmic domain comprising the ARH1 motif.

This invention further provides a method for isolating a cellular molecule capable of being a target for designing drugs for autoimmune disease, inflammation or allergy which comprises (a) contacting a cell lysate with a molecule having a motif of amino acid sequence, AENTITYSLLKHP (SEQ ID. NO:1) under the conditions permitting formation of a complex between the cellular target molecule with the motif; (b) isolating the complex formed in step (a); and (c) testing the complex for biochemical activities, thereby identifying the cellular molecule capable of being a target for designing drugs for autoimmune disease, inflammation or allergy.

Figure 1A:
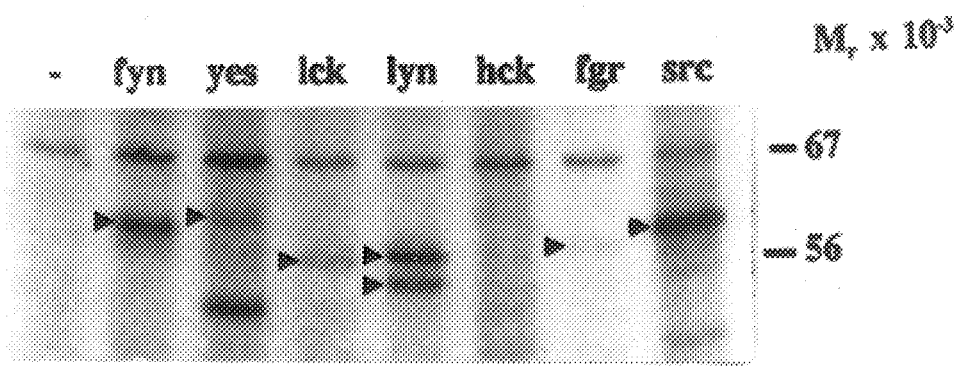
FIGS. 1A and 1B Expression and activation of $p56^{lck}$ in NK cells.

PBL, obtained by density gradient centrifugation of venous peripheral blood from healthy donors, were cultured with 30-Gy irradiated RPMI-8866 B lymphoblastoid cells. NK cells were purified from 10-d cocultures by negative selection after sensitization with anti-CD3 (OKT3), anti-CD5 (B36.1), and anti-CD14 (B52.1) monoclonal antibody (mAb) and indirect anti-globulin rosetting (7). The purity of each preparation (>95%) was confirmed in indirect immunofluorescence (flow cytometry) using a panel of mAb.

(FIG. 1A) The indicated src-related kinases (indicated by the arrowhead) were immunoprecipitated from postnuclear supernatants of NK cells lysed in 1% Triton X100, 1% sodium deoxycholate, 0.1% SDS, 150 mM NaCl, 10 mM Tris, 5 mM EDTA using protein A-Sepharose (for rabbit polyclonal antisera) or protein A-Sepharose coated with anti-mouse Ig (anti-src mAb). Precipitates were washed twice with lysis buffer and once with 100 mM NaCl, 10 mM NaCl, 10 mM Tris, pH 7.5, 5 mM $MnCl_2$. The products of in vitro kinase assays (4), performed for 15 min. on ice, were analyzed in reducing 7.5% SDS-PAGE.

(FIG. 1B) NK cells (5×10⁶/ml RPMI) were incubated for the indicated times with anti-CD16 mAb 3G8. After incubation and lysis in 1% NP-40, p56$^{lck}$ was precipitated from the postnuclear supernatants. Kinase assay was performed after addition of 1 μg enolase an the product of the kinase assay was analyzed in reducing 7.5% SDS-PAGE. No increased phosphorylation of p56$^{lck}$ or enolase was detected in p56$^{lck}$ immunoprecipitates from NK cells stimulated with anti-CD56 mAb B159.5 used as control (not shown). Anti-p56$^{lck}$ serum was produced in rabbits immunized with a synthetic peptide corresponding to amino acids 39–64 of the murine p56$^{lck}$ protein sequence (4).

FIGS. 2A–D Association of p56$^{lck}$ with FcγRIIIA in NK cells.

(FIG. 2A) FcγRIII was precipitated from NK cells (10× 10⁶ cells per precipitation) lysed in 1% digitonin, 150 mM NaCl, 20 mM Tris, pH 8.1 mM PMSF, 10 μg/ml aprotinin, 10 μg/ml leupeptin using anti-CD16 mAb 3G8, and in vitro kinase assay was performed on the immunoprecipitate. Kinase products were eluted from the beads (1% NP-40, 1 h) and the indicated proteins were precipitated using specific antibodies or normal rabbit serum (NRS) as control. Immunoprecipitates were analyzed in reducing 13% SDS-PAGE.

(FIGS. 2B–2D): Postnuclear supernatants from NK cells (50×10⁶ per precipitation), lysed as above, were precleared with goat anti-mouse:protein G for 30 min, and precipitated [Ab(1st)] with anti-CD16 mAb 3G8 or anti-CD56 mAb B159.5 coupled to goat anti-mouse Ig protein G-Sepharose was used to control (FIG. 2D) Immune complexes were washed 6 times with 0.2% digitonin lysis buffer and proteins analyzed in 7.5% reducing SDS-PAGE and Western blotting [Ab(W)] using anti-p56$^{lck}$ (rabbit polyclonal antisera, N-terminus specific, UBI, Lake Placid, N.Y.), and $^{125}$I-labeled goat anti-rabbit IgG. FIG. 2C: Postnuclear supernatants from NK cells (35×10⁶ cells per precipitation), lysed in digitonin buffer as above, were precleared (15 h) with CNBr-activated/quenched-Sepharose. Supernatants were precipitated with heat-aggregated (30 min, 63° C.) huIgG-Sepharose or F(ab')₂-Sepharose (control) for 5 h. Complexes were washed 6 times with lysis buffer and proteins analyzed on 7.5% reducing SDS-PAGE with Western blotting using anti-p56$^{lck}$ mAb (provided by Y. Koga), HRP-sheep anti-mouse Ig, and ECL. (None=lysate from approximately 10⁶ cell equivalents, no precipitation). FIG. 2D: Postnuclear supernatants from NK cells (30×10⁶ cells per precipitation), lysed in 2% NP-40, 150 mM NaCl, 20 mM Tris, 2 mM PMSF, 25 μg/ml each aprotinin, leupeptin, antipain, were precleared with protein A-Sepharose beads and incubated with rabbit antisera (anti- , anti-p56$^{lck}$, non-immune) followed by protein A-Sepharose precipitation. Beads were washed 5 times with lysis buffer and analyzed in 7.5% reducing SDS-PAGE with Western blotting for p56$^{lck}$ as in FIG. 2C. The lower bands in FIG. 2D represent rabbit IgG used for precipitation.

Figure 3A:
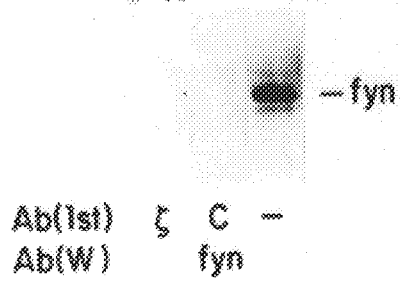
Figure 3B:
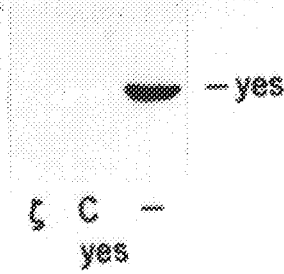
Figure 3C:
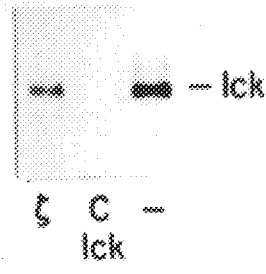
Figure 3D:
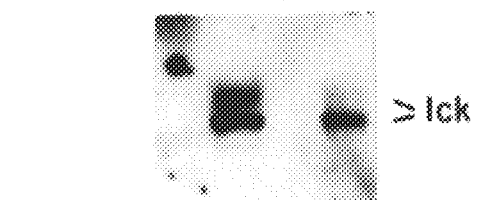

FIGS. 3A–3D. Association of p56$^{lck}$ with γ and ζ chains. COS cells were cultured in modified Eagle's medium containing 10% fetal calf serum. Mouse fyn cDNA (15) (from R. Perlmutter), human yes cDNA (16) (from T. Yamamoto and J. Sukegawa), and human lck cDNA (17) (from T. Mak) were cloned into the pCEXV-3 vector. DNA (15 μg each DNA/60 mm dish) was transfected into COS cells using the calcium-phosphate method (18) in the presence of 100 μM chloroquine. Transfected DNA are indicated at the top of each panel. The IIIA/ζ construct contained the extracellular region of FcγRIIIA and the transmembrane and cytoplasmic regions of human chain of TCR/CD3 (19). Two days after transfection, cells were solubilized in lysis buffer (3% NP-40, 50 mM Tris pH 8, 150 mM NaCl, 50 mM NaF, 10 μM molibrate, 0.2 mM vanadate, 10 μg/ml aprotinin, 10 μg/ml leupeptin, 2.5 μg/ml antipain, 0.1 mM PMSF). Cell lysates were precleared with Sepharose, incubated with the indicated Ab [Ab (1st)] coupled-Sepharose for 2 h and washed with lysis buffer 5 times. Antibodies against γ and ζ chains (19) and control antibodies were purified by protein A-Sepharose and directly coupled to CNBr-activated Sepharose. Sepharose-bound complexes were eluted into sample buffer containing 2% SDS and 1% 2-mercaptoethanol, separated in reducing 8% SDS-PAGE, and transferred to Immobilon-P sheet or nitrocellulose membrane, separated in reducing 8% SDS-PAGE, and transferred to Immobilon-P sheet or nitrocellulose membrane. Anti-fyn (UBI), anti-yes (20) (from T. Yamamoto and J. Sukegawa), and anti-lck (21) (from Y. Koga) antibodies were used for detection in Western blotting, as indicated. Filters were developed using a goat anti-rabbit or a sheet anti-mouse Ig antibody conjugated to HRP and ECL (FIGS. 3A–3C) or $^{125}$I-labeled anti-p56$^{lck}$ mAb (FIG. 3D).

Figure 4A:
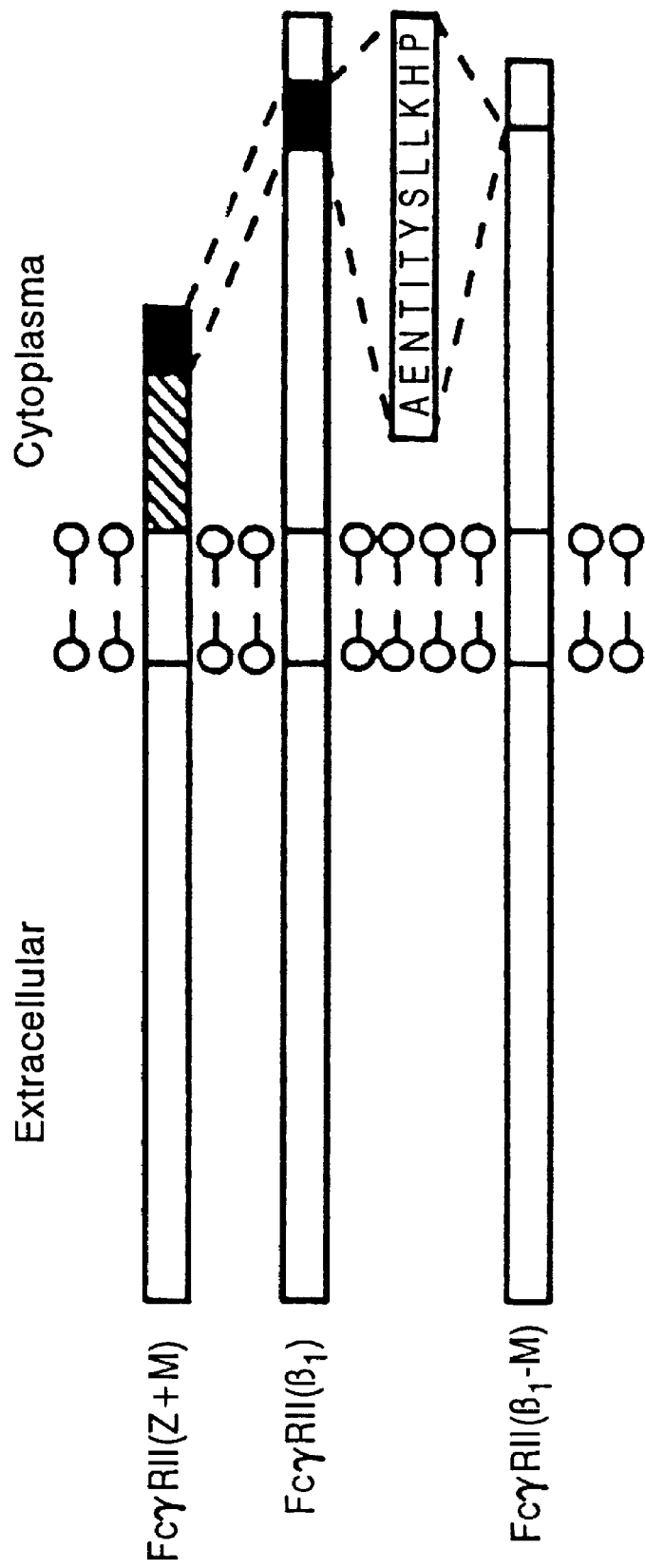
Figure 4B:
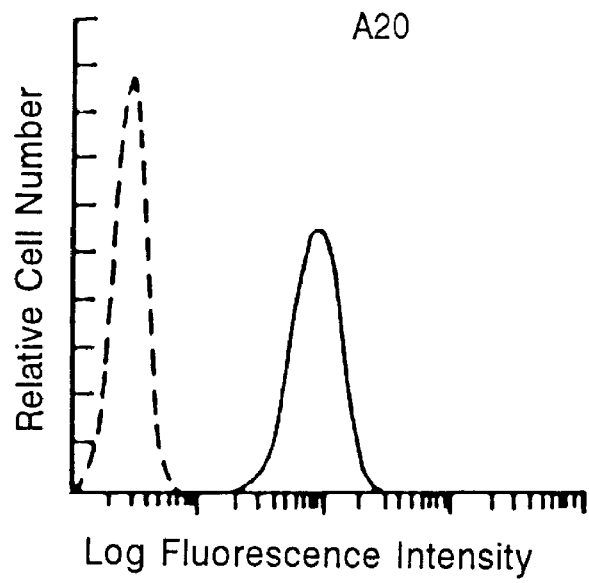
Figure 4C:
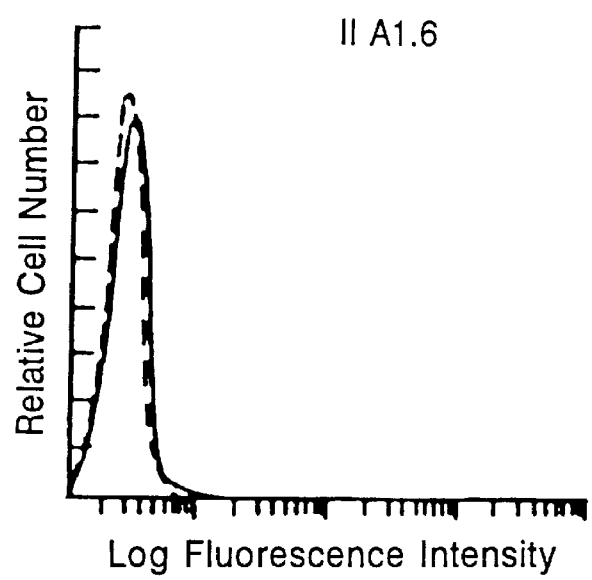
Figure 4D:
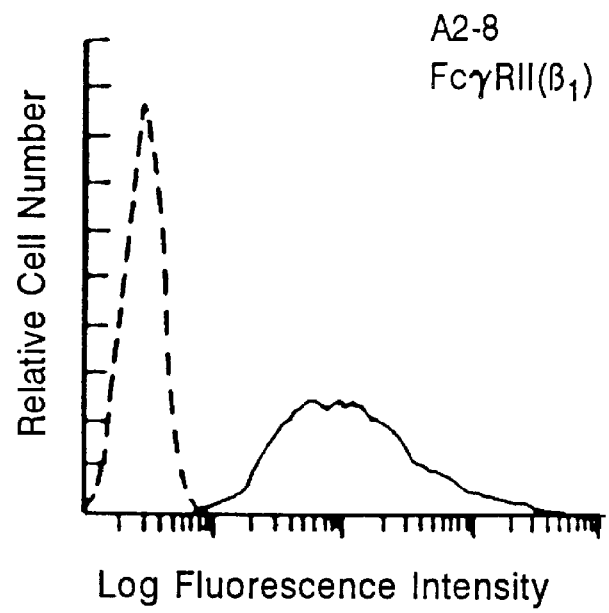
Figure 4E:
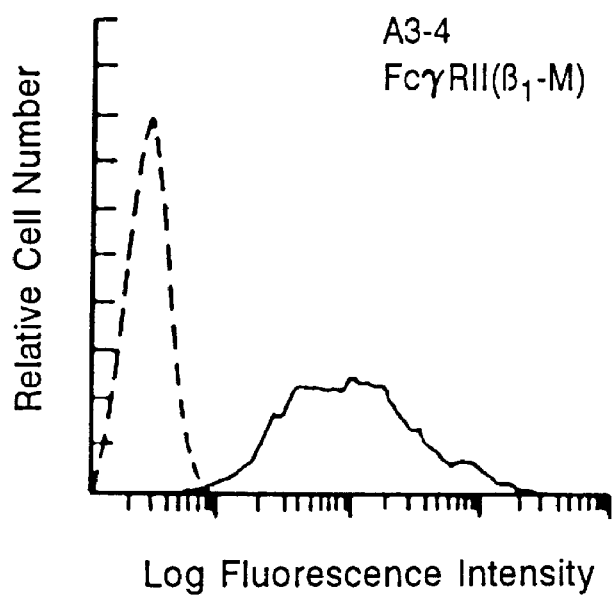
Figure 4F:
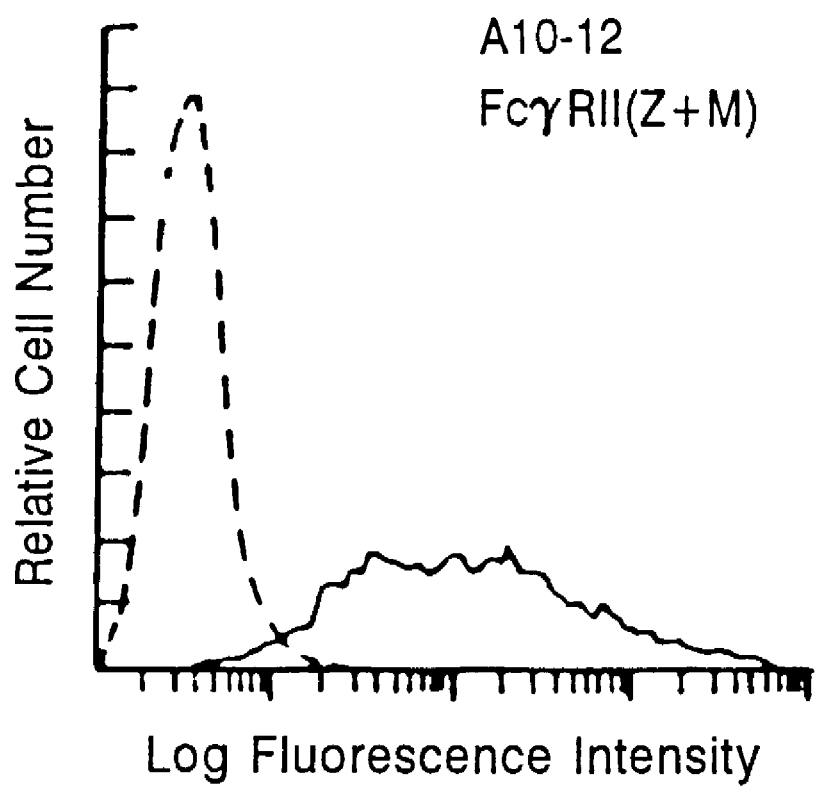
Figure 5B:
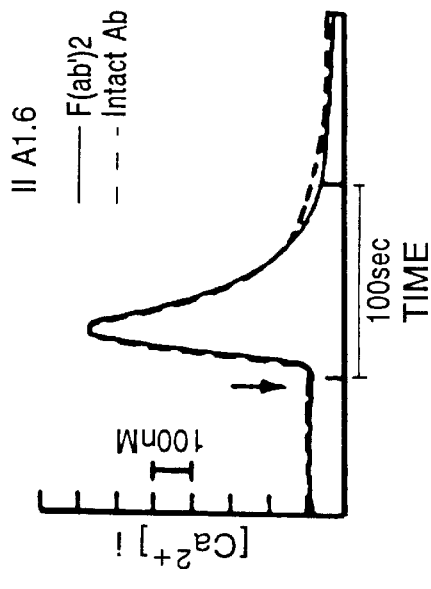
Figure 5D:
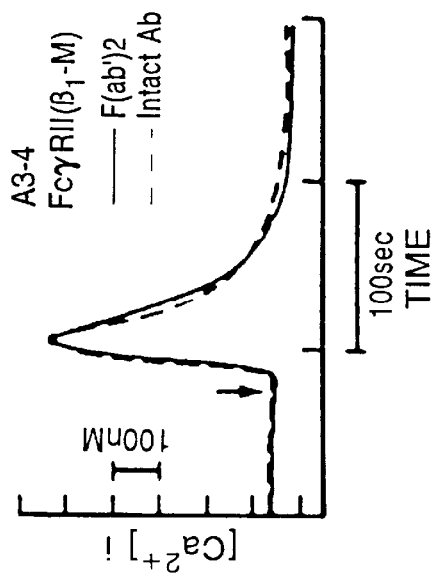
Figure 5A:
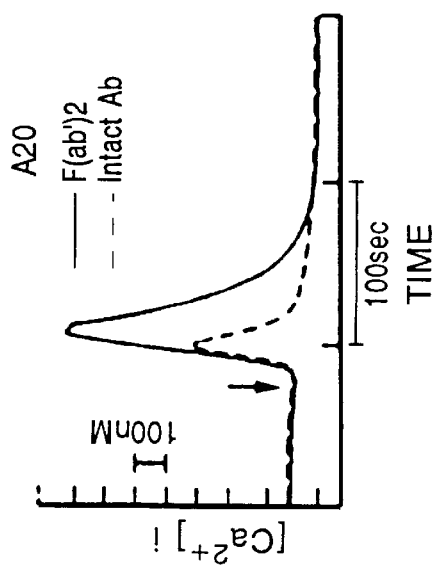
Figure 5C:
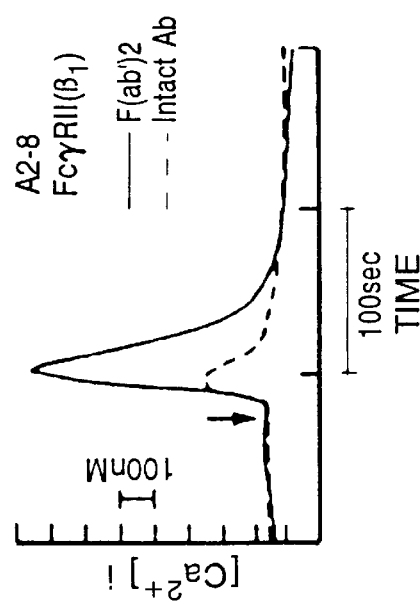
Figure 5E:
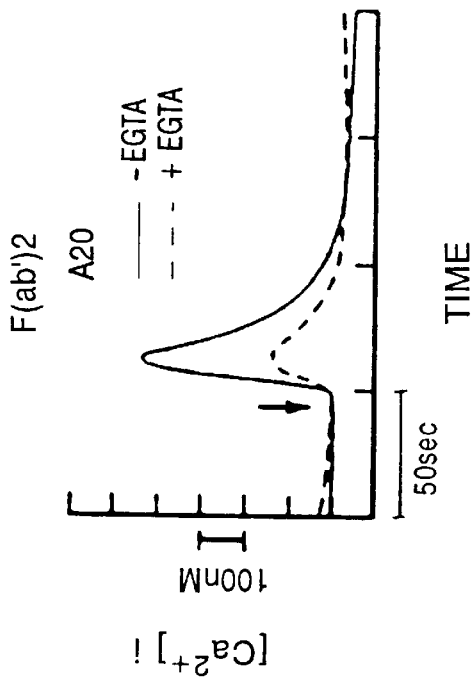
Figure 5F:
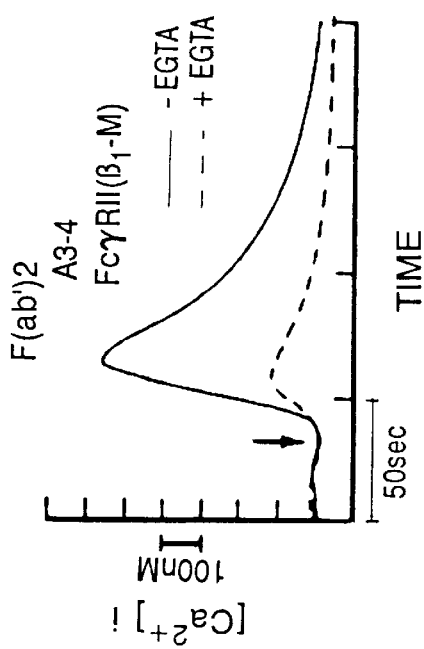
Figure 5G:
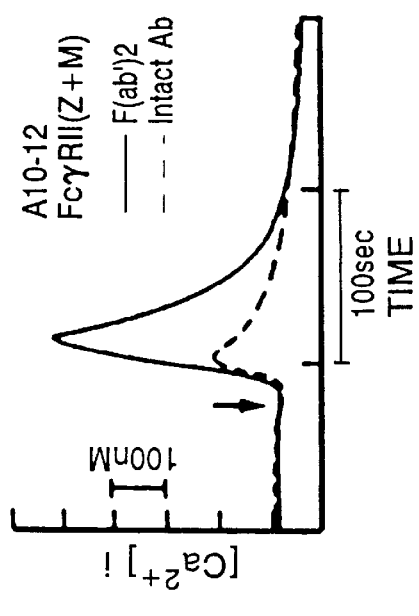
Figure 5H:
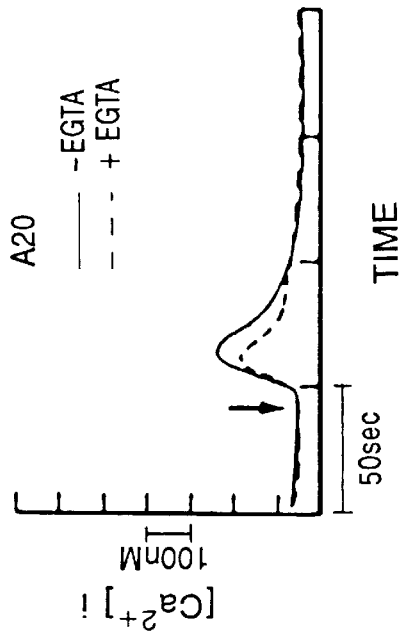
Figure 5J:
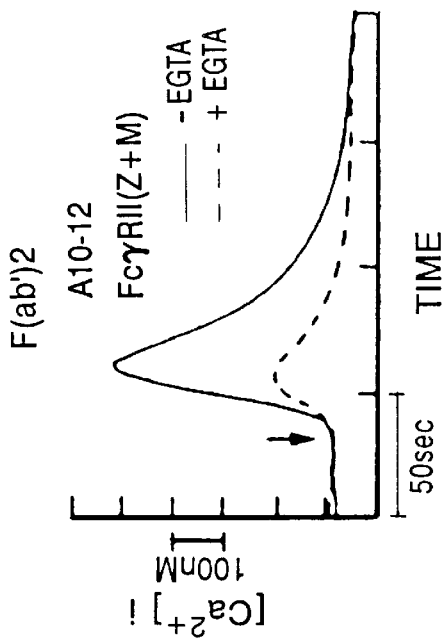
Figure 5I:
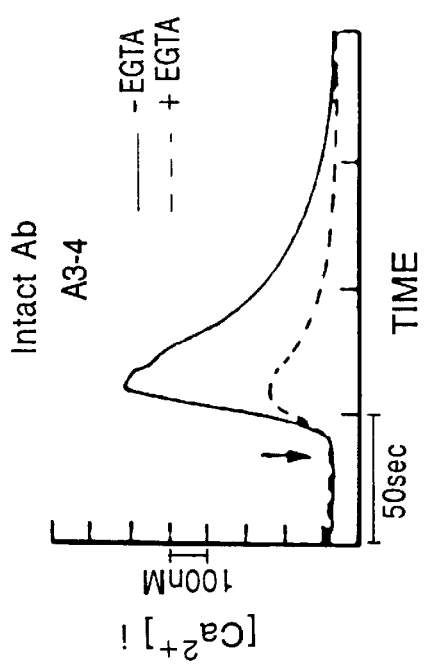
Figure 5K:
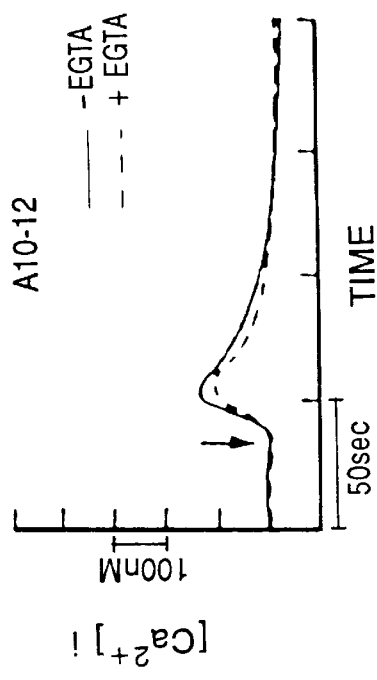
Figure 6A:
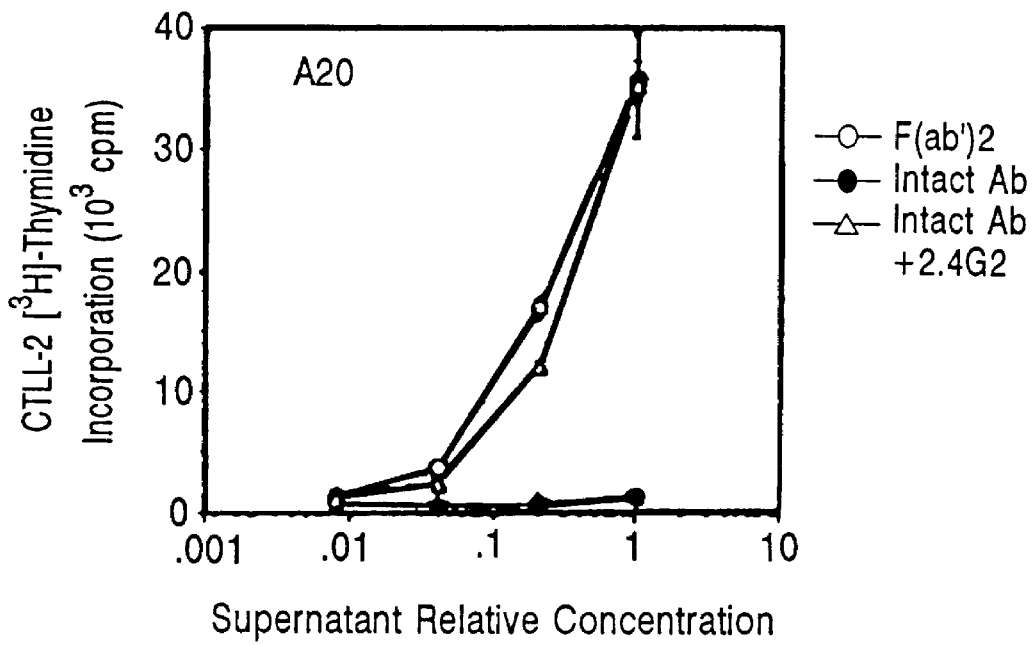
Figure 6B:
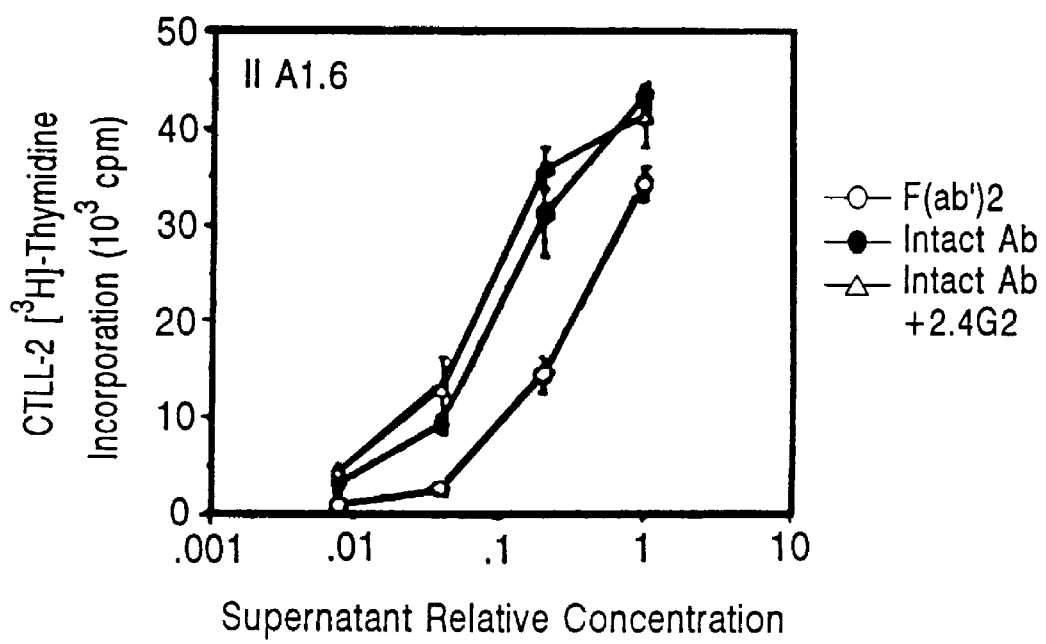
Figure 6C:
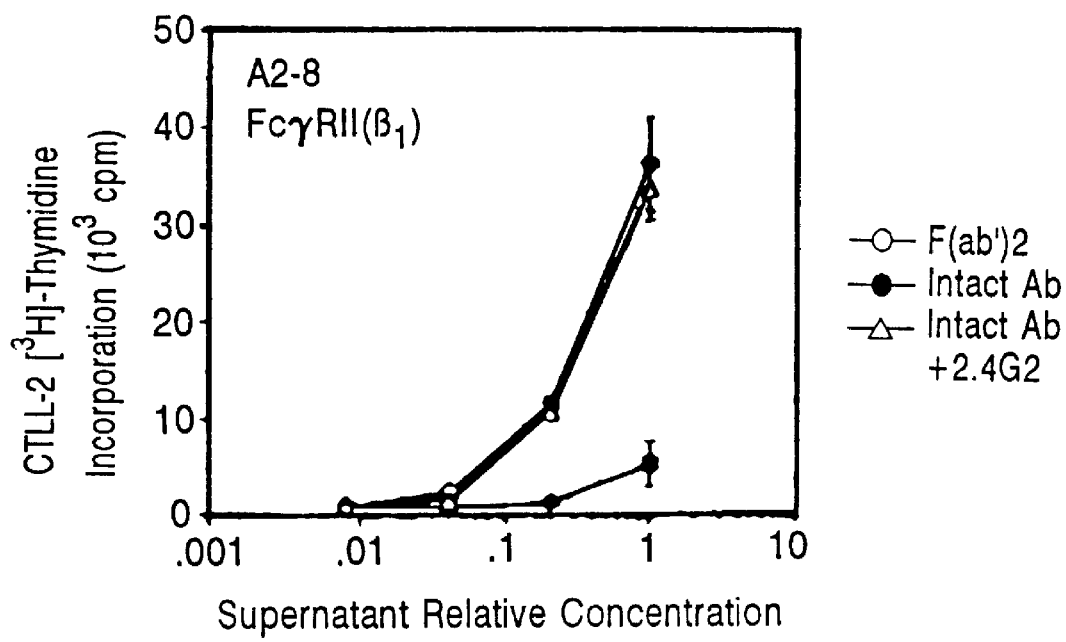
Figure 6D:
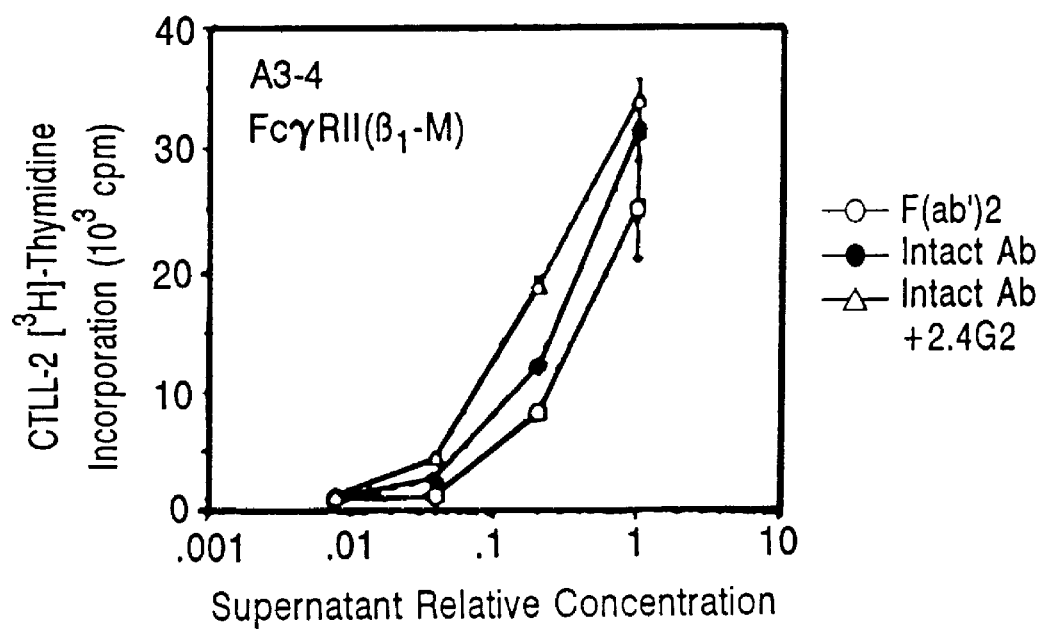
Figure 6E:
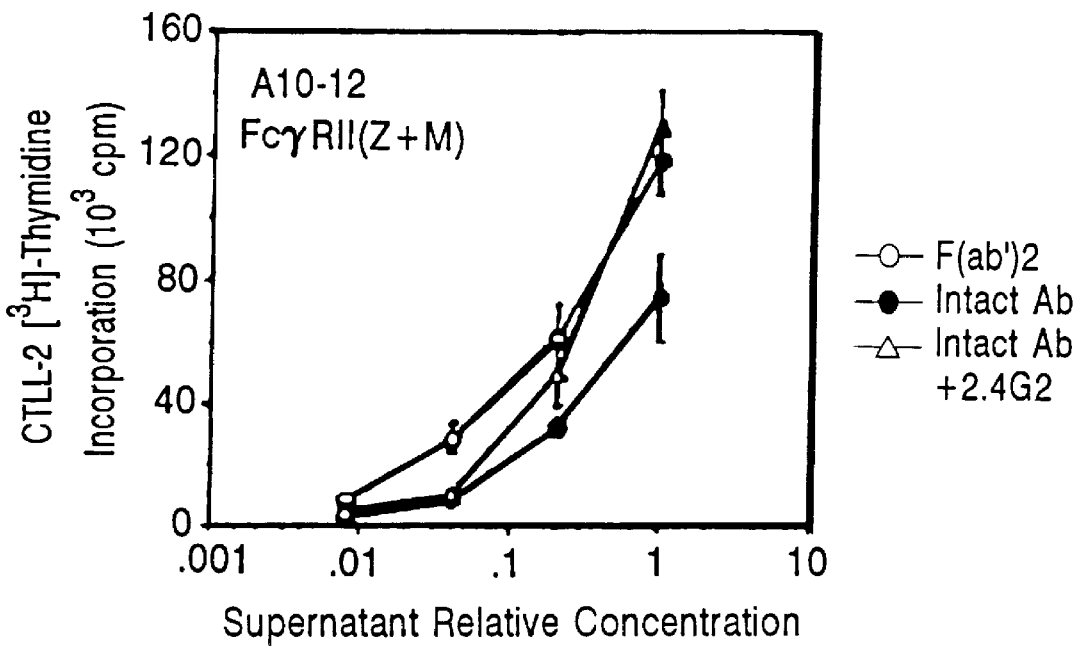
Figure 6F:
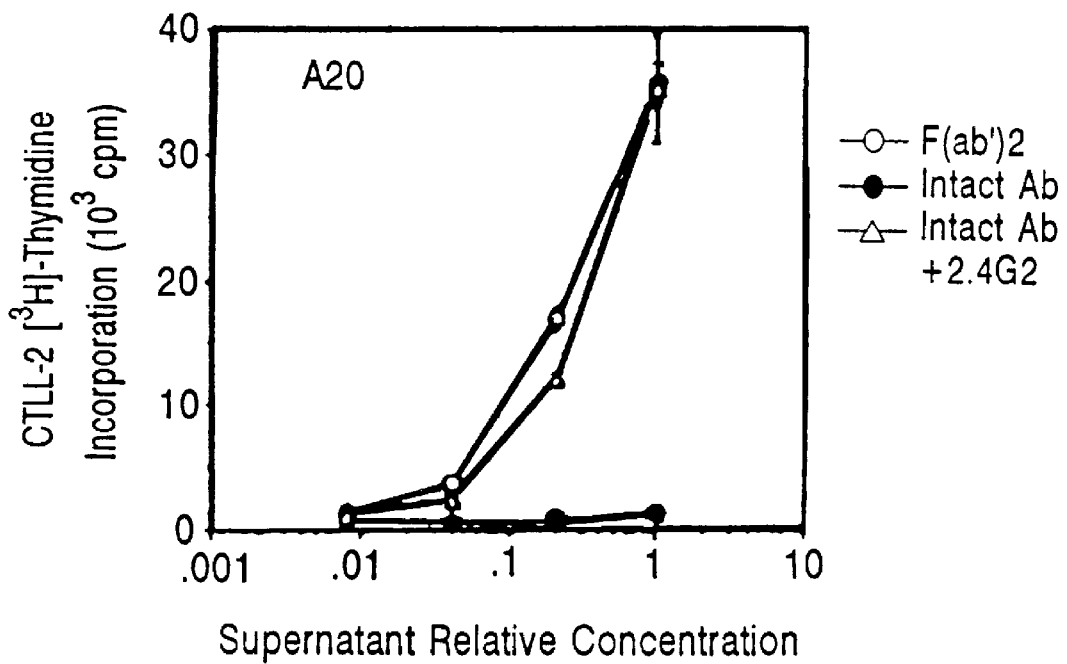
Figure 6I:
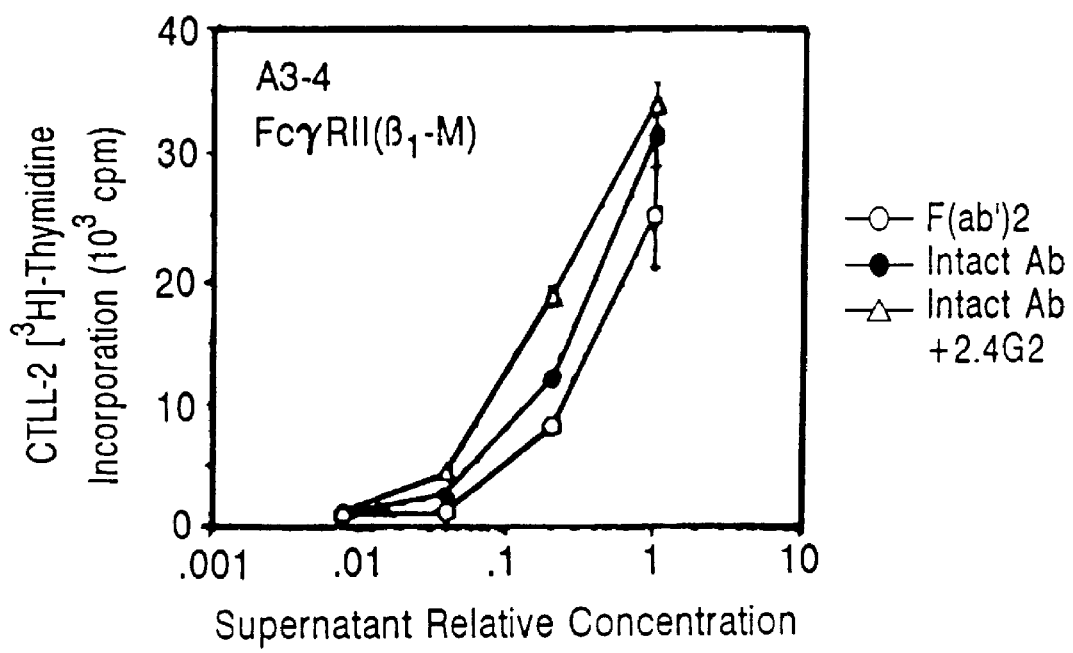

FIGS. 4A–4F Cell surface expression of mutant FcγRII Schematic representation of the mutant FcγRII FIG. 4A and FACS analysis of IIA1.6 transfected with mutant FcγRII cDNAs.

Mutant murine FcγRII cDNAs shown in FIG. 4A were constructed by using polymerase chain reaction (PCR) methods. All constructs were confirmed by sequencing. Both FcγRII(Z+M) and FcγRII(β1-M) contain the extracellular and transmembrane domains of FcγRII(β1). The cytoplasmic domain of FcγRII(β1-M) has the internal deletion of 13 residues (amino acids 303-315 in β1 isoform of FcγRII), and that of FcγRII(Z+M) is composed of the first 18 and the following 13 residues from the cytoplasmic domain of human ζ chain of TCR/CD3 (amino acids 53-68 in human ζ and two additional ser; shown in hatched region) and FcγRII (AENTITYSLLKHP), respectively. These cDNAs were cloned together with the neomycin resistant gene into pCEXV-3. IIA1.6 cells were transfected by electrophoration and neo resistant clones were checked by FACS analysis using 2.4G2 mAb.

FIGS. 5A–5K Calcium mobilization after cross-linking of mIg or co-crosslinking with FcγRII.

Ca$^{2+}$ mobilization of non-transfected and transfected cells stimulated by whole and F(ab')₂ anti-mig antibodies FIGS. 5A–5E, and the effect of EGTA on the Ca$^{2+}$ mobilization induced by these antibodies FIGS. 5F–5K.

Cells were loaded with 3 mM fura-2 and stimulated with rabbit intact (80 mg/ml) and F(ab')₂ (50 mg/ml) anti-mIgG antibodies. The application times were indicated by bars. Intracellular Ca$^{2+}$ levels were recorded with fluorescence spectrophotometer (Hitachi F2000). In the presence of 2.4G2 (4 mg/ml), Ca$^{2+}$ mobilization patterns by intact antibodies were essentially the same as those by F(ab')₂. For chelation of extracellular Ca$^{2+}$, EGTA (1 mM) was added 1 min before the ligand stimulation.

FIGS. 6A–6I IL-2 secretion after crosslinking of mIg or co-crosslinking with FcγRII.

IL-2 secretion of non-transfected and transfected cells by whole and F(ab')₂ anti-mIgG antibodies.

Cells (5×10⁵/ml) were stimulated by the indicated antibodies (10 mg/ml intact, 5 mg/ml F(ab)₂, and 10 mg/ml 2.4G2 antibodies) for 18 hr at 37° C. IL-2 activity in serial dilutions of the culture supernatant was measured by [³H]-thymidine incorporation using IL-2 dependent cell line, CTLL-2 as described. The experiments were performed three times for each cell line. The mean and SEM of triplicate points are shown.

FIGS. 7A–7H Modulation of calcium mobilization through chimeric molecules IgM/Ig-α and IgM/Ig-β by FcγRII.

Figure 7A:
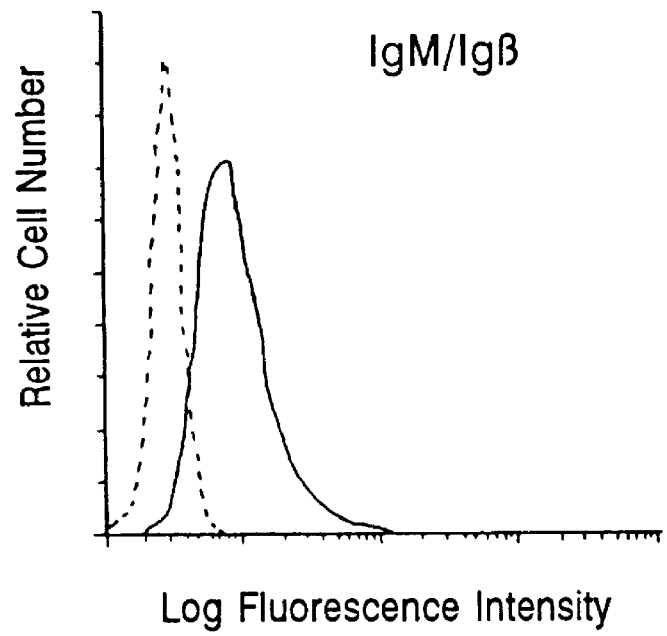
Figure 7B:
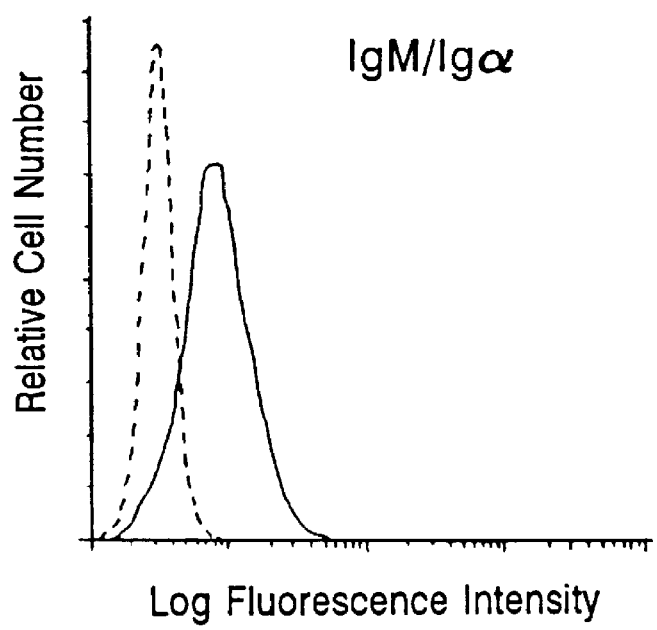
Figure 7C:
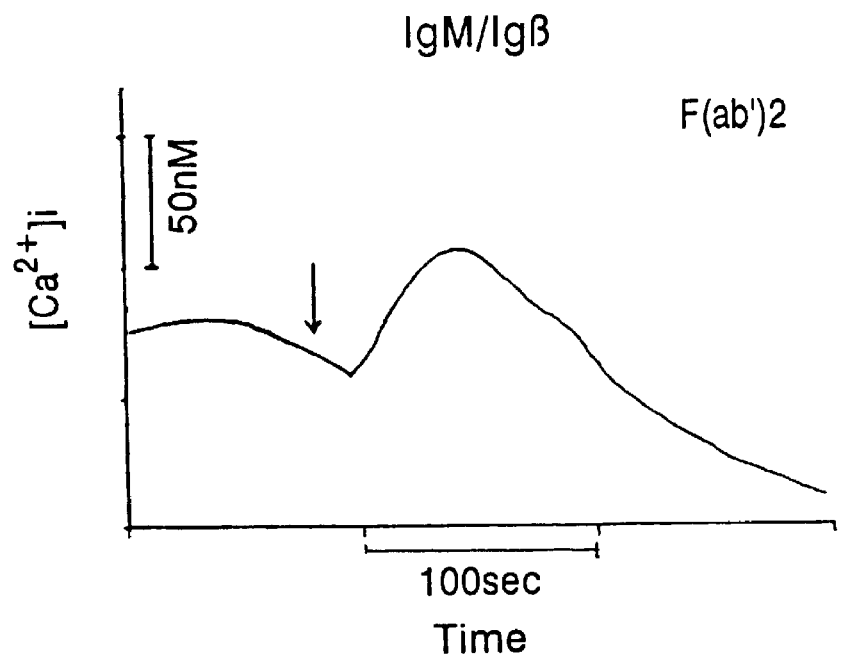
Figure 7D:
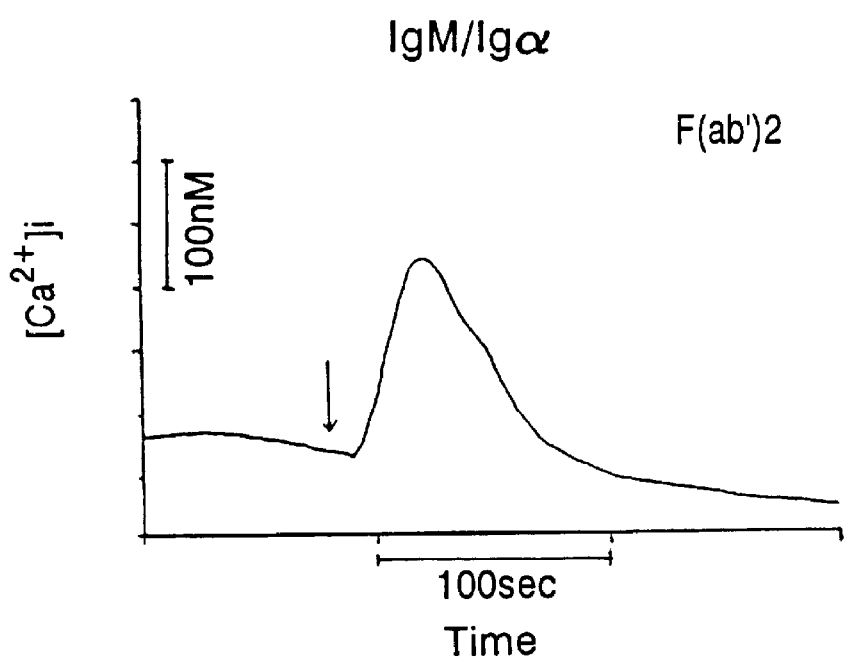
Figure 7E:
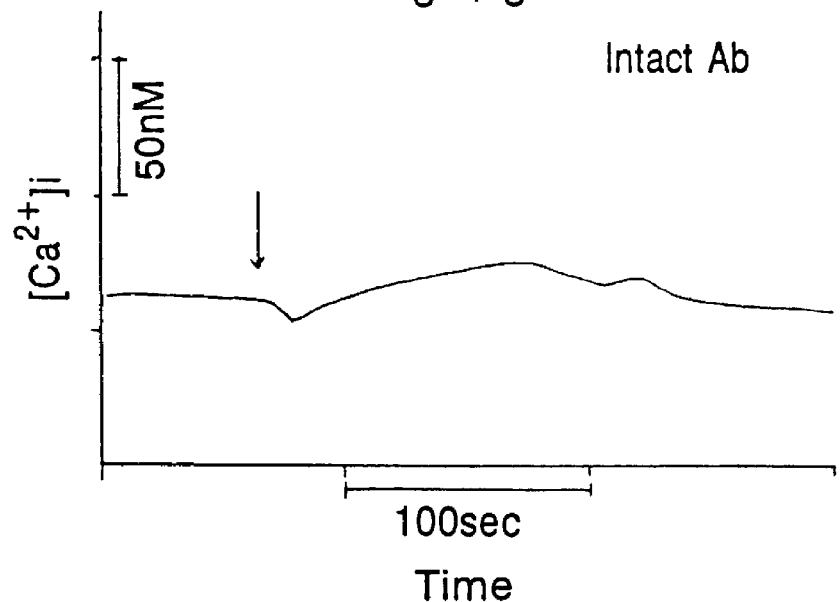
Figure 7F:
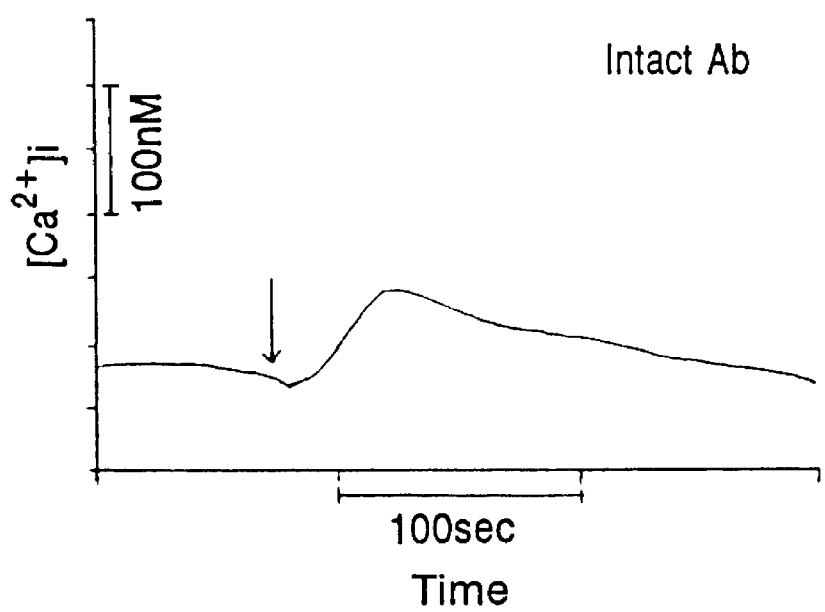
Figure 7G:
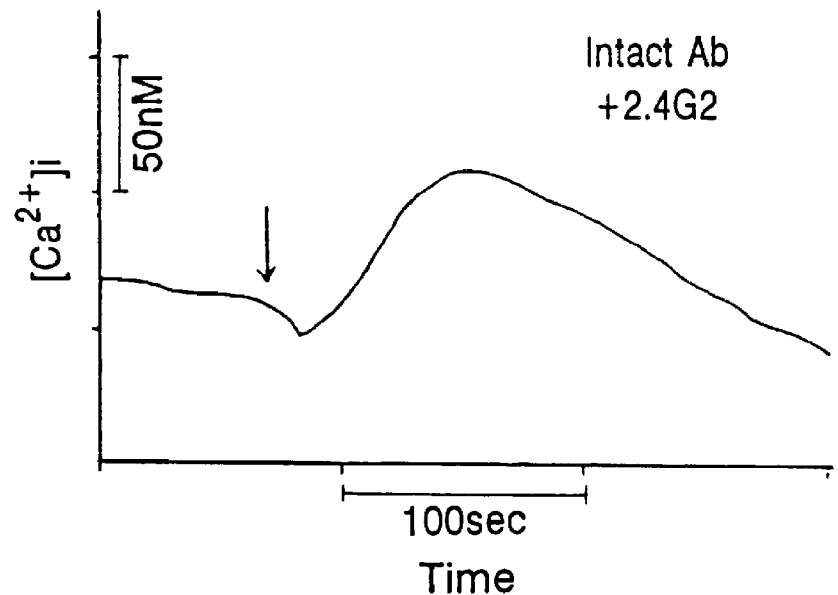
Figure 7H:
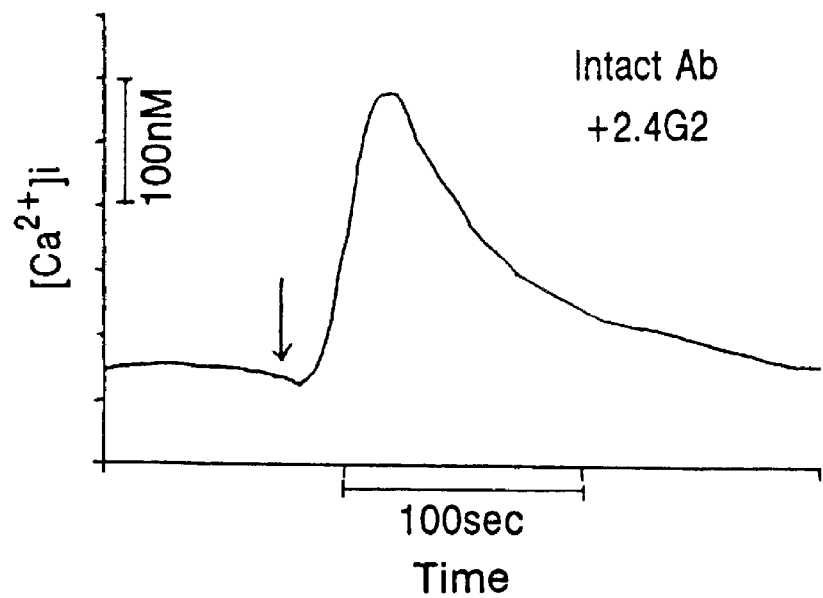

Cell surface expression of IgM/Ig-α and IgM/Ig-β on A20 cells FIGS. 7A–7B and Ca$^{2+}$ mobilization stimulated by whole and F(ab')$_2$ anti-hIgM antibodies FIGS. 7C–7H.

Chimeric IgM/Ig-α cDNA is composed of human K and μ-chimeric chains against phosphorylcholine. The extracellular, transmembrane and cytoplasmic domains of the chimeric μ chain are derived from wild-type μ chain, mutated transmembrane μ chain (replacement of both tyrosine 587, and serine 588 with valine) and murine cytoplasmic Ig-α (amino acids 160-220), respectively. IgM/Ig-β is the same as IgM/Ig-α except that the cytoplasmic domain is composed of amino acids 181-228 murine Ig-β. These cDNAs were cloned into pfNeo vector. DNAs were transfected into A20 cells by electrophoresion, and resistant clones were checked by FACS analysis using rabbit anti-hIgM antibody. Ca$^{2+}$ mobilization was examined described in FIGS. 5A–5K legends. Rabbit whole (80 mg/ml) and F(ab')$_2$ (50 mg/ml) anti-hIgM antibodies were used for stimulation (FIGS. 7E–7F and 7C–7D). Cells were preincubated with 2.4G2 (5 mg/ml) for 5 min before application of intact antibody FIGS. (7G–7H).

DETAILED DESCRIPTION OF THE INVENTION

This invention provides a method for identifying a cellular protein capable of specifically binding to an activated antibody receptor, whose cytoplasmic domain comprising an ARH1 motif, comprising (a) obtaining a cell lysate;(b) contacting the cell lysate with a molecule having an ARH1 motif under the conditions permitting formation of a complex between the cellular protein and the molecule; (c) isolating the complex formed in step (b); and (d) testing the complex for biochemical activities, thereby identifying the cellular protein capable of specifically binding to an activated antibody receptor, whose cytoplasmic domain comprising an ARH1 motif. In an embodiment, the molecule having an ARH1 motif is coupled to a matrix.

As used herein, the phrase "specifically binding" means the ability of the cellular protein to bind to the ARH1 motif specifically.

In an embodiment, the testing comprises assaying for kinase activity. In another embodiment, the testing comprises the reactivities of the complex with antibodies having known specificity.

The cellular protein identified by the above-described method can be isolated by separating the cellular protein from the complex, thereby isolating the protein capable of specifically binding to an activated antibody receptor, whose cytoplasmic domain comprising the ARH1 motif. Methods to separate a protein from a complex are well-known to a person of ordinary skill in the art.

This invention also provides a method for identifying a cellular protein capable of specifically binding to an activated antibody receptor, whose cytoplasmic domain comprising an ARH1 motif, comprising (a) obtaining cells comprising receptors having the ARH1 motif; (b) lysing the cells under conditions whereby the native complex of the receptor having the ARH1 motif and the cellular protein is preserved;(c) isolating the complex; and (d) testing the complex for biochemical activities, thereby identifying the cellular protein capable of specifically binding to an activated antibody receptor, whose cytoplasmic domain comprising an ARH1 motif. In an embodiment, cells are lysed in nonionic detergent. In a further embodiment, the nonionic detergent is digitonin.

In a preferred embodiment, the cell obtained is selected from a group consisting of natural killer cells, macrophages, neutrophils, platelet cells and mast cells.

In another embodiment, the receptors having ARH1 motif is FcγRIII, FcγRIIA, FcεRI or their subunits.

The tests for biochemical activities include, but are not limited to, assaying for kinase activity and the reactivities of the complex with antibodies having known specificity. Other methods for testing the biochemical activities for a complex known to a person of ordinary skill in the art may similarly be used.

The protein capable of specifically binding to an activated antibody receptor, whose cytoplasmic domain comprising the ARH1 motif may be isolated by separating the cellular protein from the complex.

This invention further provides a method of stimulating a natural killer cell, a macrophage, a neutrophil, a platelet cell or a mast cell comprising introducing to the cell an amount of lck protein or analog thereof effective to stimulate the cell.

As used in this invention, lck protein or analog include fragments or derivatives of antigenic polypeptides which differ from naturally-occurring forms in terms of the identity or location of one or more amino acid residues (deletion analogs containing less than all of the residues specified for the protein, substitution analogs wherein one or more residues specified are replaced by other residues and addition analogs where in one or more amino acid residues is added to a terminal or medial portion of the polypeptides) and which share some or all properties of naturally-occurring forms.

This invention also provides a method of stimulating a natural killer cell, a macrophage, a neutrophil, a platelet or a mast cell in a subject comprising introducing to the cell an amount of lck protein or analog thereof effective to stimulate the cell in the subject.

This invention provides an pharmaceutical composition comprising an inhibitor of the above described complex or lck protein and a pharmaceutically acceptable carrier. In an embodiment, the complex possess kinase activity and therefore, the inhibitor may be a kinase inhibitor. In another embodiment, the inhibitor may be a peptide containing the ARH1 sequence of its analog. The peptide will be able to compete with the complex for the binding of the cellular protein, thereby inhibiting the activity of the complex.

In another embodiment, the cellular protein in the complex is identified as the lck protein and therefore, inhibitor to this particular tyrosine kinase may be used. Other inhibitors of tyrosine kinase if they are found in the complex may be used for this invention.

This invention provides a method of inhibiting the stimulation of a natural killer cell, a macrophage, a neutrophil, a platelet cell or a mast cell comprising introducing an amount of the above pharmaceutical composition effective to inhibit the stimulation of a natural killer cell, a macrophage, a neutrophil, a platelet cell or a mast cell.

This invention also provides a method of inhibiting the stimulation of a natural killer cell, a macrophage, a neutrophil, a platelet cell or a mast cell in a subject comprising administering to the subject an amount of the above-described pharmaceutical composition effective to inhibit the stimulation of a natural killer cell, a macrophage, a neutrophil, a platelet cell or a mast cell in the subject.

This invention provides a method of treating inflammation in a subject comprising administering to the subject an amount of the above-described pharmaceutical composition effective to inhibit stimulation of a natural killer cell, a macrophage, a neutrophil, a platelet cell or a mast cell, thereby treating inflammation in the subject.

This invention provides a method of treating allergy in a subject comprising administering to the subject an amount of the above-described pharmaceutical composition effective to inhibit stimulation of a natural killer cell, a macrophage, a neutrophil, a platelet cell or a mast cell, thereby treating allergy in the subject.

This invention further provides a method for isolating a cellular molecule capable of being a target for designing drugs for autoimmune disease, inflammation or allergy which comprises (a) contacting a cell lysate with a molecule having a motif of amino acid sequence, AENTITYS-LLKYHP (SEQ ID. NO:1) under the conditions permitting formation of a complex between the cellular molecule with the motif; (b) isolating the complex formed in step (a); and (c) testing the complex for biochemical activities, thereby identifying the cellular protein capable of specifically binding to an activated antibody receptor, whose cytoplasmic domain comprising the ARH1 motif. In an embodiment, the molecule having an AENTITYSLLKHP (SEQ ID. NO:1) motif is coupled to a matrix.

The testing for biochemical activities includes but is not limited to assaying for kinase activity and the reactivities of the complex with antibodies having known specificity. Other ways to test for biochemical activities of a complex are well-known to a person of ordinary skill in the art.

The cellular protein may be separated from the complex, thereby isolating the cellular molecule for anti-inflammatory or allergic agent.

This invention further provides a method for isolating a cellular molecule capable of being a target for designing drugs for autoimmune disease, inflammation or allergy which comprises (a) obtaining cells with a molecule having a motif of amino acid sequence, AENTITYSLLKHP; (SEQ ID. NO:1) (b) lysing the obtained cells under conditions thereby the native complex of the endogenous molecule having the AENTITYSLLKHP (SEQ ID. NO:1) motif and the cellular target molecule is preserved; (c) testing the complex with different biochemical activities, thereby identifying the cellular molecule capable of specifically binding to an activated antibody receptor, whose cytoplasmic domain comprising the AENTITYSLLKHP (SEQ ID. NO:1) motif.

Various type of testing methods may be used for identifying the protein in the complex. For example, the complex may be assayed for kinase activity or reactivities of the complex with antibodies having known specificity.

Alternatively, this cellular protein may be separated from the complex, thereby isolating the cellular molecule capable of being a target for designing drugs for autoimmune disease, inflammation or allergy using standard methods. The biochemical and biophysical properties of the isolated protein can then be further characterized.

This invention further provides an pharmaceutical composition comprising the AENTITYSLLKHP (SEQ ID. NO:1) peptide or analog thereof or an inhibitor of the above-described complex of the AENTITYSLLKHP (SEQ ID. NO:1) motif and a cellular molecule and a pharmaceutically acceptable carrier.

As used herein, analogs of the AENTITYSLLKHP (SEQ ID. NO:1) peptide should possess the same biological activity as the AENTITYSLLKHP (SEQ ID. NO:1) peptide. Methods to modify a peptide to generate functional analogs are well-known in the art. A person of ordinary skilled in the art can easily modify the AENTITYSLLKHP (SEQ ID. NO:1) sequence directly by chemical methods or generate another peptide substituted with other amino acids but still having the biological or functional activity of the AENTITYSLLKHP (SEQ ID. NO:1) peptide.

This invention provides a method of inhibiting the stimulation of a B-lymphocyte, a natural killer cell, a macrophage, a neutrophil, a platelet cell or a mast cell comprising introducing an amount of the above pharmaceutical composition effective to inhibit the stimulation of a B-lymphocyte, a natural killer cell, a macrophage, a neutrophil, a platelet cell or a mast cell.

This invention provides a method of inhibiting the stimulation of a B-lymphocyte, a natural killer cell, a macrophage, a neutrophil, a platelet cell or a mast cell in a subject comprising administering to the subject an amount of the above pharmaceutical composition effective to inhibit the stimulation of a B-lymphocyte, a natural killer cell, a macrophage, a neutrophil, a platelet cell or a mast cell in the subject.

This invention provides a method of treating autoimmune disease in a subject comprising administering to the subject an amount of the above pharmaceutical composition effective to inhibit stimulation of a B-lymphocyte, a natural killer cell, a macrophage, a neutrophil, a platelet cell or a mast cell, thereby treating inflammation in the subject.

This invention provides a method of treating inflammation in a subject comprising administering to the subject an amount of the pharmaceutical composition of claim 10 effective to inhibit stimulation of a B-lymphocyte, a natural killer cell, a macrophage, a neutrophil, a platelet cell or a mast cell, thereby treating inflammation in the subject.

This invention provides a method of treating allergy in a subject comprising administering to the subject an amount of the above pharmaceutical composition effective to inhibit stimulation of a lymphocyte, a natural killer cell, a macrophage, a neutrophil, a platelet cell or a mast cell, thereby treating allergy in the subject.

The discovery of short amino acid sequence motifs involved in signal transduction from a variety of inflammatory receptors (FcRs) and the cellular targets which interact with them; methods for detecting these interactions in vivo and in vitro and methods for detecting the description of these interactions.

This invention is useful as a method for identifying compounds which prevent inflammatory signalling from natural killer cells macrophages, neutrophils, platelet cells and mast cells.

The problem which this invention solves is specific inhibitors of allergic reaction, rheumatic inflammations, natural killer cell mediated rejection.

This invention will be better understood from the Experimental Details which follow. However, one skilled in the art will readily appreciate that the specific methods and results discussed are merely illustrative of the invention as described more fully in the claims which follow thereafter.

EXPERIMENTAL DETAILS

First Series of Experiments

FcγRIIIA (CD16) binds IgG immune complexes with low affinity and mediates the antibody-dependent cytotoxicity of NK cells (1). This receptor is a multimeric complex composed of three functionally and biochemically distinct proteins: IIIAα, a 254 amino acid transmembrane-spanning glycoprotein containing the extracellular ligand binding domain, IIIAγ and IIIAζ, membrane-spanning subunits responsible for both assembly and signal transduction (1). The γ and ζ chains are members of a family of homologous proteins present as homo- or heterodimers, first described as subunits of the high affinity Fc receptor for IgE, FcεRI, and of the T cell antigen receptor/CD3 (TCR/CD3) complex (2). Ligand binding and crosslinking of FcγRIII induce NK cell activation with release of intracytoplasmic granules and upregulation of genes encoding surface activation molecules and cytokines relevant to NK cell biology and functions (3). The early biochemical events induced in NK cells upon engagement of FcγRIII include tyrosine phosphorylation of intracellular substrates ζ and γ chains, phospholipase C (PLC)-γ1 and PLC-γ2, phosphatidylinositol-3 (PI-3) kinase], hydrolysis of membrane phosphoinositides ($PIP_2$), increased $[Ca^{2+}]_i$ and activation of PI-3 kinase (4). The observation that treatment of NK cells with tyrosine kinase inhibitors blocks both FcγRIII-induced hydrolysis of membrane $PIP_2$ and subsequent increase in $[Ca^{2+}]$, (4) and later activation events (5) has indicated the involvement of a tyrosine kinase(s) in initiating and/or mediating FcγRIII which could account for its ability to activate cells upon crosslinking. Results from experiments with chimeric molecules containing and γ cytoplasmic domains linked with extracellular domains of heterologous molecules support the hypothesis that a non-receptor kinase(s) associates with FcγRIII possibly via the γ or ζ subunits (6). In cells expressing these chimeric molecules, stimulation of the extracellular domains results in signal transduction.

We set out to determine how FcγRIII stimulates protein tyrosine phosphorylation in NK cells by testing the hypothesis that FcγRIII interacts directly with protein tyrosine kinases in these cells.

Figure 1B:
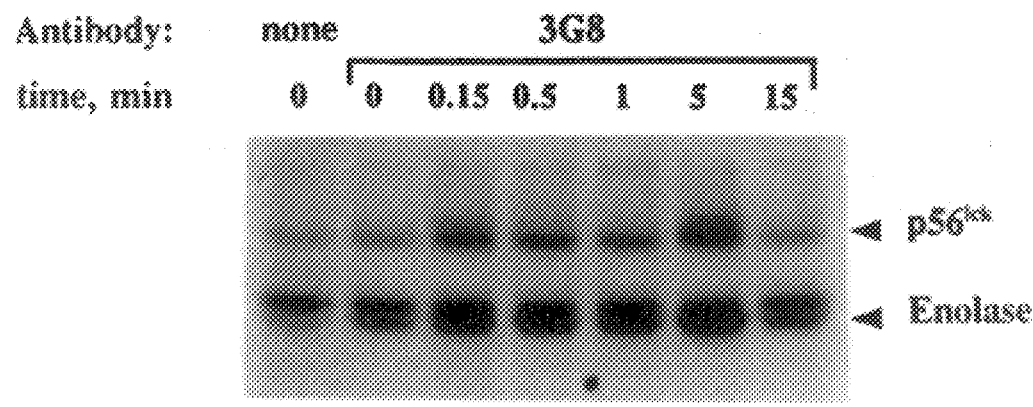

Expression of src-related kinases was analyzed in homogeneous NK cell populations obtained from short term (10 d) cocultures of peripheral blood lymphocytes (PBL) with irradiated RPMI-8866 B lymphoblastoid cells (7). The NK cell preparations are >95% homogeneous and have phenotypic and functional properties identical to those of freshly isolated NK cells except that they express late activation antigens and are more readily activatable (7). These NK cells expressed several src-related tyrosine kinases, including $p53^{lyn}$ and $p56^{lyn}$, $p56^{lck}$, p60, and $p62^{fyn}$, as measured by kinase-autophosphorylation in immune-complex protein kinase assays (FIG. 1A). Upon stimulation of FcγRIII with the anti-receptor monoclonal antibody 3G8, we detected a rapid activation of at least one of the src-related kinases, $p56^{lck}$, that was rapidly activated, as analyzed by in-vitro kinase assay on $p56^{lck}$ immunoprecipitates isolated from cells after receptor stimulation (FIG. 1B). Increased $p56^{lck}$ autophosphorylation and phosphorylation of the exogenous substrate enolase was detected as early as 10 s after receptor stimulation. These results are consistent with those we previously reported using CD3 Jurkat cells expressing transfected FcγRIIIAα chain in association with endogenous (4), and indicate that $p56^{lck}$ is functionally associated with FcγRIII in primary NK cells.

Figure 2A:
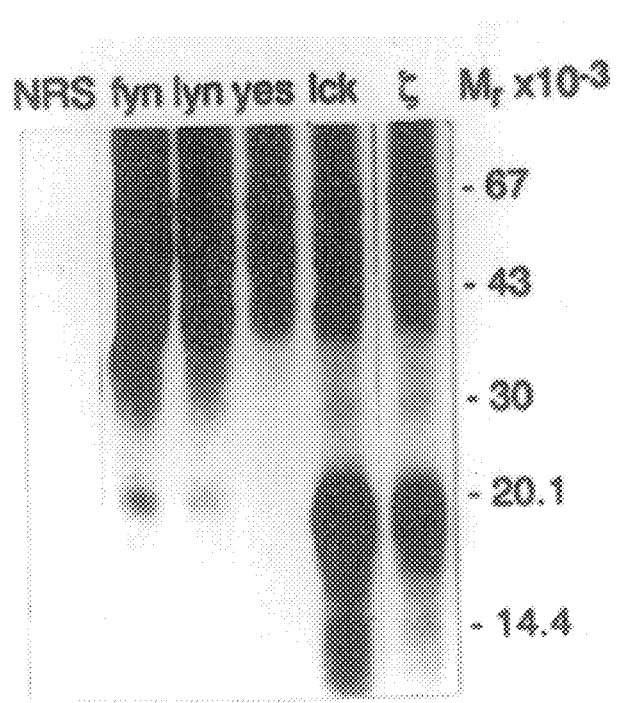

To determine how $p56^{lck}$ is stimulated upon FcγRIII crosslinking, we precipitated the receptor from digitonin lysates of NK cells and assayed for tyrosine kinase activity in the immunoprecipitates. Tyrosine kinase activity was coprecipitated with FcγRIII and resulted in the phosphorylation of the chain subunit. Phosphorylated chain was preferentially observed within the FcγRIII immunoprecipitate when reprecipitated with anti-$p56^{lck}$ or anti-antibodies (FIG. 2A). These data clearly indicate that is a substrate for $p56^{lck}$-dependent tyrosine phosphorylation and strongly suggest that $p56^{lck}$ coprecipitates with FcγRIII. To determine directly whether $p56^{lck}$ and FcγRIII are physically associated, anti-$p56^{lck}$ immunoblotting was performed on immunoprecipitates isolated from NK cells using FcγRIII ligands on NK cells were solubilized in 1% digitonin to preserve the association of FcγRIIIA subunits. $p56^{lck}$ was specifically detected in immunoprecipitates isolated with either anti-receptor antibody (3G8) (FIG. 2B) or the natural ligand immune complexes (heat-aggregated IgG) (FIG. 2C). Aggregates lacking Fc did not yield $p56^{lck}$ complexes, and isotype-matched anti-CD56 antibodies yielded significantly lower amounts of them. Western blot analysis with an anti-CD16 rabbit polyclonal antibody confirmed that both FcγRIIIAα and chain are present in the 3G8 and the aggregated IgG, but not in the F(ab')$_2$ precipitates (data not shown). The stoichiometry of the FcγRIII-$p56^{lck}$ association appears low: ≦1% of total cellular $p56^{lck}$ was coprecipitated with FcγRIII (FIG. 2C). Similar low levels of association have been reported between TcR and tyn in T cells (8) and may reflect instability of receptor subunits upon detergent extraction. Increased $p56^{lck}$-FcγRIII association could not be demonstrated upon receptor crosslinking (data not shown).

To directly assess which FcγRIII subunit is responsible for the association with $p56^{lck}$, anti $p56^{lck}$ immunoblotting experiments were performed on immunoprecipitates isolated with anti-polyclonal antisera. NK cells were lysed in 2% NP-40 to reduce possible nonspecific precipitation of $p56^{lck}$. Using a large number of NK cells and a sensitive detection system (Enhanced Chemiluminescence, ECL) a small fraction of total cellular $p56^{lck}$ was detected in the anti-precipitates (FIG. 2D; compare anti-$p56^{lck}$ precipitates with anti-ζ). In addition, a phosphoprotein with molecular mass similar to phospho-ζ(~21 kD) was detected in the respective $p56^{lck}$ immunoprecipitates isolated from either digitonin- and, to a lesser extent, NP-40-solubilized NK cells as analyzed by in vitro kinase assays (not shown).

To confirm that $p56^{lck}$ associates with and to determine whether this association is direct or is, in part, mediated by additional proteins, experiments were performed using COS cells cotransfected with various src-family related kinase cDNA (mouse fyn, human yes, and human lck) and a cDNA encoding a chimeric protein composed of the extracellular region of FcγRIIIAα and the transmembrane and cytoplasmic regions of human ζ (IIIA/ζ). Transfected cells were lysed in 3% NP-40, immunoprecipitates were collected using either anti-antibody coupled-Sepharose or control antibody-Sepharose and subjected to immunoblotting with the respective anti-src-related kinase antibody. Coprecipitation of IIIA/and $p56^{lck}$, but not fyn or yes (FIGS. 3A–3C) or src (not shown), was detected. Similar experiments in COS cells cotransfected with $p56^{lck}$ and γ cDNAs revealed association of these two proteins, although to levels lower than those observed with (FIG. 3D).

Our results indicate that the src-related kinase $p56^{lck}$ associates both functionally and physically with the FcγRIIIA complex on NK cells. This association appears to be mediated in part via the chain. The results of ζ/γ/$p56^{lck}$ cotransfection experiments in COS cells prove that $p56^{lck}$ and either ζ or γ subunits can associate via direct interaction. Although the molecular basis of the association remains to be determined, it is likely to depend, in part, on the antigen receptor homology 1 motifs (ARH1) of ζ/γ which are conserved sequences [(ASP or GLU)-$X_7$-(ASP or GLU)-TYR-X-LEU-$X_7$-TYR-$X_2$-(LEU or ILE (SEQ ID. NO:2–9))] found in many receptor signal transducing chains, including TCRζ, η, γ, and ε, FcεRI β and γ chains, B cell antigen receptor chains Ig-α (mb1) and Ig-β (B29), and human FcγRIIA (9). Evidence to support the contention that these sequences mediate coupling of receptors to signaling pathways has been provided for the B cell antigen receptor chains Ig-α and Ig-β (10). Differential binding patterns of the ARH1 regions in these proteins for cytoplasmic effectors were observed, indicating that the presence of an ARH1 motif is insufficient for binding cytoplasmic effector molecules but that additional chain-specific residues determine binding specificity and a single motif can bind more than one effector molecule (10). Our preliminary data indicate that the p56$^{lck}$-ζ interaction depends on the presence of ARH1 motifs in, and deletion of one or more of them results in a proportionally decreased association (not shown). This may also explain, in part, the detection of lower levels of p56$^{lck}$ associated with γ chain (a single ARH1 motif) as compared to ζ((3 ARH1 motifs). The p56$^{lck}$ domain involved in this interaction has not been defined. It is likely to differ from that involved in the interaction between p56$^{lck}$ and CD4, shown to depend on the NH$_2$-terminal sequence of this molecule (11), because no sequence homology is found between the ARH1 motif and CD4.

Functional interaction between p56$^{lck}$ and the ζ/γ subunit is supported by observations in T cells. Elegant studies using p56$^{lck}$-deficient cell lines (which endogenously express fyn) strongly support a role for p56$^{lck}$ in signal transduction via the TCR and in cell-mediated cytotoxic responses (12). Cytotoxic functions are restored upon re-expression of p56$^{lck}$ and, most interestingly in regard to NK cells, appear independent of CD4 or CD8 engagement (12). Although our cotransfection experiments in COS cells demonstrate a direct interaction of p56$^{lck}$ and ζ/γ, additional proteins may be necessary to mediate optimal association or disassociation of these two molecules in primary cells. The situation in NK cells may be analogous to that observed in T cell lines. A 70 kD protein (ZAP-70) has been observed to associate with ζ in the Jurkat T cell line upon TCR/CD3 stimulation (13). Proteins of similar size are rapidly phosphorylated upon engagement of the B cell antigen receptor complex (p72$^{syk}$), the FcεRI complex (14), and FcγRIII in NK cells (4, and our unpublished data). Although the role of these 70–72 kD proteins/kinases is unknown, they may function to stabilize the primary interaction of ARH1 containing subunits with src-related protein tyrosine kinases.

REFERENCES AND NOTES OF THE FIRST SERIES OF EXPERIMENTS

1. J. V. Ravetch and J. P. Kinet, *Annu. Rev Immunol.* 9, 457 (1991).
2. D. G. Orloff, C. Ra, S. J. Frank, R. D. Klausner, J. P. Kinet, *Nature* 347, 189 (1990).
3. I. Anegon, M. C. Cuturi, G. Trinchieri, B. Perussia, *J. Exp. Med* 167, 452 (1988); M. C. Cuturi et al., *J. Exp. Med.* 169, 569 (1989).
4. L. Azzoni, M. Kamoun, T. Salcedo, P. Kanakaraj, B. Perussia, *J. Exp. Med* in press (1992); M. A. Cassatella et al., *J. Exp. Med.* 169, 549 (1989); P. Kanakaraj et al., in preparation.
5. J. J. O'Shea, D. W. McVicar, D. B. Kuhns, J. R. Ortaldo, *J. Immunol.* 148, 2497 (1992).
6. B. A. Irving and A. Weiss, *Cell* 64, 891 (1991); Romeo and Seed, *Cell* 64, 1037 (1991); F. Letourneur and R. D. Klausner, *Proc. Natl. Acad. Sci.* 88, 8905 (1991); E. Eiseman and J. B. Bolen, *J. Biol. Chem.* 267, 21027 (1992); C. Romeo, M. Amiot, B. Seed, *Cell* 68, 889 (1992).
7. B. Perussia et al., *Nat. Immun. and Cell Growth Regul.* 6, 171 (1987).
8. L. E. Samelson, A. F. Phillips, E. T. Loung, R. D. Klausner, *Proc. Natl. Acad. Sci. U.S.A.* 87, 4358 (1990).
9. M. Reth, *Nature* 338, 383 (1989); A. M. K. Wegener et al., *Cell* 68, 83 (1992).
10. M. R. Clark et al., *Science* 258, 123 (1992).
11. A. S. Shaw et al., *Cell* 59, 627 (1989); J. M. Turner et al., ibid. 60, 755 (1990); A. S. Shaw et al., *Mol. Cell. Biol.* 10, 1853 (1990).
12. D. B. Straus and A. Weiss. *Cell* 70, 585 (1992); L. Karnitz et al., *Molec. and Cellul. Biol.* 12, 4521 (1992).
13. A. C. Chan, B. A. Irving, J. D. Fraser, A. Weiss, *Proc. Natl. Acad. Sci. U.S.A.* 88, 9166 (1991); R. L. Wange, A. N. Tony Kong, L. E. Samelson, *J. Biol. Chem.* 267, 11685 (1992).
14. J. E. Hutchcroft, M. L. Harrison, R. L. Geahlen, *J. Biol. Chem.* 266, 14846 (1991); J. E. Hutchcroft, R. L. Geahlen, G. G. Deanin, J. M. Oliver, *Proc. Natl. Acad. Sci. U.S.A.* 89, 9107 (1992).
15. M. P. Cooke and R. M. Perlmutter, *New Biol.* 1, 66 (1989).
16. J. Sukegawa et al., *Molec. Cellul. Biol.* 7, 41 (1987).
17. Y. Koga et al., *Eur. J. Immunol.* 16, 1643 (1986).
18. M. Mishina et al., *EMBO J.*, 1, 1533 (1982).
19. T. Kurosaki, I. Gander, J. V. Ravetch, *Proc. Natl. Acad. Sci. USA* 88, 3837 (1991).
20. J. Sukegawa et al., *Oncogene* 5, 611 (1989).
21. Y. Mori et al., *Japan J. Cancer Res.* 82, 909 (1991).

Second series of experiments

Surface immunoglobulin complex is composed of antigen recognition substructure, membrane immunoglobulin (mIg) and associated signal transduction subunit, Ig-α (mb-1) and Ig-β (B29). These mig-associated chains contain within their cytoplasmic domains a conserved motif of six precisely spaced amino acids, the antigen receptor homology 1 motif (ARH1), which carries sufficient structural information to activate signaling pathways. Engagement of the surface immunoglobulin complex trigger B-cell differentiation and proliferation through activation of tyrosine kinase(s), mobilization of intracellular Ca$^{2+}$, and activation of protein kinase C. Crosslinking FcγRII with the surface immunoglobulin complex confers a dominant inhibition signal that prevents or aborts the activation. Here, we show that FcgRII modulates mIg induced Ca$^{2+}$ mobilization by inhibiting Ca$^{2+}$ influx from the outside, whereas the activation pattern of tyrosine phosphorylation is not altered by the cross-linking FcγRII with mIg. A 13 residue motif of the cytoplasmic domain of FcγRII was able to be appended to the intracellular domain of other proteins to inhibit the Ca$^{2+}$ mobilization upon the stimulation of the mIg. Calcium mobilization induced by chimeric IgM/Ig-α and IgM/Ig-β molecules in which thecytoplasmic domain of mIgM were substituted with the corresponding Ig-α and Ig-β, was modulated by the cross-linking FcγRII with these receptors. These data suggest that the 13 residue motif in FcγRII modulates the Ca$^{2+}$ signaling activated by the ARH1 motif in Ig-α and Ig-β subunits of surface immunoglobulin complex.

FcγRII (β1 isoform) is expressed at high levels on B cells where they are involved in modulating B cell activation by surface immunoglobulin complex. Typically, cross-linking of mIg by antigen or anti-Ig F(ab')$_2$ antibody induces a transient increase in cytosolic free Ca$^{2+}$, a rise in inositol-3-phosphate (IP$_3$), activation of protein kinase C and enhanced protein tyrosine phosphorylation. We tested which proximal events induced by the stimulation of mIg is inhibited by the crosslinking FcgRII together with mIg. By adding anti-mIg (whole IgG directed towards the mIg), which cross-linked surface FcγRII with mIg, inhibited the Ca$^{2+}$ mobilization in the A20 B-lymphoma cell line (FIGS. 5A–5E). This inhibition was reversed in the presence of 2.4G2 mAb which prevented the binding of the intact Fc domain of the anti-mig to FcγRII (data not shown). Stimulation of mIg evokes both Ca$^{2+}$ release from intracellular stores and Ca$^{2+}$ influx from the outside. To distinguish which Ca$^{2+}$ movements is modulated by cross-linking FcγRII with mIg, A20 cells were stimulated in the presence or absence of EGTA. EGTA incubation decreased the Ca$^{2+}$ mobilization upon the cross-linking of mIg with anti-mIg F(ab')$_2$ almost 4-fold, whereas even in the presence of EGTA, Ca$^{2+}$ mobilization induced by adding whole anti-mIg was almost the same (FIGS. 5F–5K). This result indicates that the Ca$^{2+}$ modulation by FcγRII is primarily due to the inhibition of Ca$^{2+}$ influx across the plasma membrane. Comparison of tyrosine phosphorylated proteins of A20 cell lysates stimulated by whole or F(ab')$_2$ anti-mIg antibody showed no significant change. And also we did not detect difference of the stimulation of tyrosine phosphorylation of phospholipase C-γ1 by whole or F(ab')$_2$ antibodies (data not shown). Since phospholipase C-γ1 is presumably involved in IP$_3$ formation, and IP$_3$ induces the Ca$^{2+}$ mobilization from the intracellular compartment, this observation supports the previous conclusion that FcγRII modulates mainly Ca$^{2+}$ influx from the outside upon the engagement of mIg.

To define the functional region(s) within the FcγRII cytoplasmic domain responsible for inhibition signal of Ca$^{2+}$ mobilization via membrane immunoglobulin complex, cDNA encoding 13 residues internal deletion of FcγRII cytoplasmic domain was transfected into IIA1.6 cell line, FcγRII negative mutant of the A20 B-cell lymphoma (FIG. 4A). The designated clone was selected based on high level of surface expression assayed by flow cytometry (FIGS. 4B–5F). In contrast to the wild type of FcγRII, this internal deletion mutant showed no modulation of Ca$^{2+}$ influx by cross-linking FcγRII together with mIg (FIGS. 5A–5E). To determine whether this 13 residue segment of FcgRII cytoplasmic domain is sufficient to inhibit the Ca$^{2+}$ mobilization, the fusion construct in which the first 18 residue and the following 13 residue of the cytoplasmic domain, are derived from the ζ chain of TCR/CD3 complex and FcγRII respectively (FIG. 4A), was transfected into IIA1.6 cell line. This fusion receptor was able to inhibit the Ca$^{2+}$ mobilization by cross-linking FcgRII with mIgG and also this modulation was due to blocking the Ca$^{2+}$ influx from the outside the cells (FIGS. 5A–5K). These results demonstrate that the 13 residue motif in the cytoplasmic domain of FcγRII has a sufficient structural information to inhibit mIg induced Ca$^{2+}$ mobilization.

As late responses, we analyzed the effect of the 13 residue segment of FcγRII on the modulation IL-2 secretion via mIg. As expected, wild type FcγRII modulated IL-2 secretion by crosslinking FcγRII with mIgG, whereas the 13 residue deleted FcγRII abolished this modulation. The fusion receptor FcγRII(Z+M) showed the significant modulation, however compared with the wild type FcγRII, the modulation extent was almost half (FIGS. 7A–7H). This weak modulation by FcγRII(Z+M) was not due to the cell surface density of FcγRII(Z+M), shown by flow cytometric analysis (FIGS. 4B–4F). These results suggest that the 13 residue segment in the cytoplasmic domain of FcγRII is required for the modulation of late responses, but for complete modulation of late responses, possibly other cytoplasmic region(s) of FcγRII is also necessary.

Surface immunoglobulin complex is composed of membrane immunoglobulin (mIg) and associated signal transduction subunit Ig-α (mb1) and Ig-β (B29). The ARH1 motif located in the cytoplasmic domain of these associated chains was shown to carry sufficient structural information to activate signaling pathway. However, recent in vitro and in vivo experiments have demonstrated that the cytoplasmic domains of Ig-α and Ig-β interact with different cytoplasmic effector proteins, resulting in the differential biological capability. To asses directly whether FcgRII modulates Ig-α and Ig-β dependent signaling, the chimeric IgM/Ig-α and IgM/Ig-β constructs in which the extracellular and transmembrane domains are derived from mIgM and the cytoplasmic domain from Ig-α and Ig-β, were transfected into A20 B cell lymphoma. To avoid the association of these chimeric molecules with endogenous Ig-α and Ig-β, we introduced the mutations (tyr-ser to val-val) in the transmembrane domain of mIgM. It was already shown that the introduction of non-polar groups such as val-val in place of tyr-ser in the transmembrane domain of mIgM produces a receptor that can no longer associate with Ig-α and Ig-β. Even though the cell surface expression of IgM/Ig-α and IgM/Ig-β was not so high (FIGS. 7A and 7B), crosslinking of these chimeric molecules with anti-IgM F(ab')$_2$ evoked Ca$^{2+}$ mobilization.

Crosslinking FcγRII with IgM/Ig-α and IgM/Ig-β inhibited this Ca$^{2+}$ mobilization and in the presence of 2.4G2, this inhibition was reversed (FIGS. 7B–7H). These results indicate that FcγRII prevents mIgM induced Ca$^{2+}$ activation presumably through the ADH1 motif located in the cytoplasmic domain of Ig-α and Ig-β.

It is well known that the early biochemical events induced in B cells upon engagement of surface lmmunoglobulin complex include tyrosine phosphorylation of intracellular substrates, hydrolysis of phosphoinositides, increased intracellular Ca$^{2+}$. Although there are several suggestions that FcγRII interacts with elements in the mIg signaling pathway, the molecular nature of the inhibitory FcγRII-mediated signal on B cell activation is unknown. Our results show that Ca$^{2+}$ influx across the plasma membrane induced by mIg is primarily inhibited by the cross-linking FcγRII together with mIg. The Ca$^{2+}$ mobilization from the intracellular compartment is not modulated. This conclusion is strengthened by the observation that stimulation of tyrosine phosphorylated of PLC-γ1 and IP$_3$ turnover was not modulated by the crosslinking FcγRII with mIg. Any significant difference of induction of tyrosine phosphorylation by assessing the cell lysates with anti-phosphotyrosine antibody, was not detected, suggesting that FcγRII does not modulate overall induction of tyrosine phosphorylation by engagement of surface immunoglobulin complex.

The results presented here suggest that the active site of FcγRII to inhibit mIg-induced Ca$^{2+}$ mobilization is a 13 residue short linear peptide sequence. It appears likely that the interaction of this motif with one or at most few proteins suffices to mediate Ca$^{2+}$ modulation.

Since recent reports showed that the interaction of SH2 containing proteins with peptides is through phosphotyrosine and isoleucine binding pockets spaced by two amino acids, next focus will be destined to the involvement of phosphotyrosine included in this 13 residue motif.

As a simple model system, we transfected IgM/Ig-α and IgM/Ig-β chimeric molecule whose ADH1 motif in the cytoplasmic domains of Ig-α and Ig-β is presumably involved solely in the receptor activation. Ca$^{2+}$ mobilization induced by these chimeric molecules was significantly modulated by cross-linking FcγRII with IgM/Ig-α and IgM/Ig-β, indicating that FcγRII inhibit both Ig-α and Ig-β dependent Ca$^{2+}$ signaling.

What is claimed is:

1. A method for isolating a cellular molecule capable of being a target for designing drugs for treating autoimmune disease, inflammation or allergy which comprises
    (a) contacting a cell lysate with a molecule having an amino acid sequence, ARNTITYSLLKHP (SEQ ID. NO:1) under the conditions permitting formation of a complex between the cellular target molecule with the amino acid sequence AENTITYSLLKHP;
    (b) isolating the complex formed in step (a); and
    (c) testing the complex for biochemical activities, thereby identifying the cellular molecule capable of being a target for designing drugs for treating autoimmune disease, inflammation or allergy.

2. The method of claim 1, wherein the molecule having an amino acid sequence AENTITYSLLKHP is coupled to a matrix.

3. The method of claim 1, wherein the testing comprises assaying for kinase activity.

4. The method of claim 1, wherein the testing comprises the reactivities of the complex with antibodies having known specificity.

5. The method of claim 1, further comprising separating the cellular protein from the complex, thereby isolating the cellular target molecule for anti-inflammatory or allergic agent.

6. A method for isolating a cellular molecule capable of being a target for designing drugs for treating autoimmune disease, inflammation or allergy which comprises
    (a) obtaining cells with a molecule having an amino acid sequence, AENTITYSLLKHP (SEQ ID. NO:1);
    (b) lysing the obtained cells under conditions whereby the native association of the endogenous molecule having the amino acid sequence AENTITYSLLKHP and the cellular target molecule is preserved;
    (c) testing the complex for different biochemical activities, thereby identifying the cellular molecule capable of being a target for designing drugs for treating autoimmune disease, inflammation or allergy.

7. The method of claim 6, wherein the testing comprises assaying for kinase activity.

8. The method of claim 6, wherein the testing comprises the reactivities of the complex with antibodies having known specificity.

9. The method of claim 6, further comprising separating the cellular protein from the complex, thereby isolating the cellular molecule capable of being a target for designing drugs for autoimmune disease, inflammation or allergy.

* * * * *

UNITED STATES PATENT AND TRADEMARK OFFICE
CERTIFICATE OF CORRECTION

PATENT NO.   :   5,824,487
DATED        :   October 20, 1998
INVENTOR(S)  :   Jeffrey V. RAVETCH and Tomohiro KUROSAKI It is certified that errors appear in the above-identified patent and that said Letters Patent is hereby corrected as shown below:

Foremost page, Related U.S. Application Data, [63], Continuation of Serial No. "08/052,269" Should be - - 08/052,267- -.

Signed and Sealed this

Fifteenth Day of May, 2001

Attest:

NICHOLAS P. GODICI

Attesting Officer    Acting Director of the United States Patent and Trademark Office

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:1:

```
Ala  Glu  Asn  Thr  Ile  Thr  Tyr  Ser  Leu  Leu  Lys  His  Pro
1                  5                            10
```

( 2 ) INFORMATION FOR SEQ ID NO:2:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:2:

```
Asp  Xaa  Xaa  Xaa  Xaa  Xaa  Xaa  Xaa  Asp  Tyr  Xaa  Leu  Xaa  Xaa  Xaa  Xaa
1                  5                            10                           15
Xaa  Xaa  Xaa  Tyr  Xaa  Xaa  Leu
                20
```

( 2 ) INFORMATION FOR SEQ ID NO:3:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:3:

```
Asp  Xaa  Xaa  Xaa  Xaa  Xaa  Xaa  Xaa  Asp  Tyr  Xaa  Leu  Xaa  Xaa  Xaa  Xaa
1                  5                            10                           15
Xaa  Xaa  Xaa  Tyr  Xaa  Xaa  Ile
                20
```

( 2 ) INFORMATION FOR SEQ ID NO:4:

( i ) SEQUENCE CHARACTERISTICS:
        ( A ) LENGTH: 23 amino acids
        ( B ) TYPE: amino acid
        ( C ) STRANDEDNESS: single (D) TOPOLOGY: linear (i i) MOLECULE TYPE: protein (i i i) HYPOTHETICAL: NO (i v) ANTI-SENSE: NO (x i) SEQUENCE DESCRIPTION: SEQ ID NO:4:

```
Asp Xaa Xaa Xaa Xaa Xaa Xaa Xaa Glu Tyr Xaa Leu Xaa Xaa Xaa Xaa
1               5                   10                  15
Xaa Xaa Xaa Tyr Xaa Xaa Leu
            20
```

(2) INFORMATION FOR SEQ ID NO:5:

(i) SEQUENCE CHARACTERISTICS:
  (A) LENGTH: 23 amino acids
  (B) TYPE: amino acid
  (C) STRANDEDNESS: single
  (D) TOPOLOGY: linear (i i) MOLECULE TYPE: protein (i i i) HYPOTHETICAL: NO (i v) ANTI-SENSE: NO (x i) SEQUENCE DESCRIPTION: SEQ ID NO:5:

```
Asp Xaa Xaa Xaa Xaa Xaa Xaa Xaa Glu Tyr Xaa Leu Xaa Xaa Xaa Xaa
1               5                   10                  15
Xaa Xaa Xaa Tyr Xaa Xaa Ile
            20
```

(2) INFORMATION FOR SEQ ID NO:6:

(i) SEQUENCE CHARACTERISTICS:
  (A) LENGTH: 23 amino acids
  (B) TYPE: amino acid
  (C) STRANDEDNESS: single
  (D) TOPOLOGY: linear (i i) MOLECULE TYPE: protein (i i i) HYPOTHETICAL: NO (i v) ANTI-SENSE: NO (x i) SEQUENCE DESCRIPTION: SEQ ID NO:6:

```
Glu Xaa Xaa Xaa Xaa Xaa Xaa Xaa Asp Tyr Xaa Leu Xaa Xaa Xaa Xaa
1               5                   10                  15
Xaa Xaa Xaa Tyr Xaa Xaa Leu
            20
```

(2) INFORMATION FOR SEQ ID NO:7:

(i) SEQUENCE CHARACTERISTICS:
  (A) LENGTH: 23 amino acids
  (B) TYPE: amino acid
  (C) STRANDEDNESS: single
  (D) TOPOLOGY: linear (i i) MOLECULE TYPE: protein (i i i) HYPOTHETICAL: NO (i v) ANTI-SENSE: NO (x i) SEQUENCE DESCRIPTION: SEQ ID NO:7:

```
Glu Xaa Xaa Xaa Xaa Xaa Xaa Xaa Asp Tyr Xaa Leu Xaa Xaa Xaa Xaa
```

-continued

```
         1                   5                          1 0                           1 5

Xaa  Xaa  Xaa  Tyr  Xaa  Xaa  Ile
                      2 0
```

( 2 ) INFORMATION FOR SEQ ID NO:8:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:8:

```
   Glu  Xaa  Xaa  Xaa  Xaa  Xaa  Xaa  Xaa  Glu  Tyr  Xaa  Leu  Xaa  Xaa  Xaa  Xaa
   1                   5                          1 0                           1 5

Xaa  Xaa  Xaa  Tyr  Xaa  Xaa  Leu
                      2 0
```

( 2 ) INFORMATION FOR SEQ ID NO:9:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:9:

```
   Glu  Xaa  Xaa  Xaa  Xaa  Xaa  Xaa  Xaa  Glu  Tyr  Xaa  Leu  Xaa  Xaa  Xaa  Xaa
   1                   5                          1 0                           1 5

Xaa  Xaa  Xaa  Tyr  Xaa  Xaa  Ile
                      2 0
```